United States Patent
Hulvershorn et al.

(10) Patent No.: US 12,397,134 B2
(45) Date of Patent: Aug. 26, 2025

(54) SYSTEMS, METHODS, AND DEVICES FOR FACILITATING ACCESS TO TARGET ANATOMICAL SITES OR ENVIRONMENTS

(71) Applicant: Medline Industries, LP, Northfield, IL (US)

(72) Inventors: Justin Hulvershorn, Seattle, WA (US); Karl Schmidt, Seattle, WA (US); Douglas Swartz, Seattle, WA (US)

(73) Assignee: Medline Industries, LP, Northfield, IL (US)

( * ) Notice: Subject to any disclaimer, the term of this patent is extended or adjusted under 35 U.S.C. 154(b) by 1159 days.

(21) Appl. No.: 16/582,013

(22) Filed: Sep. 25, 2019

(65) Prior Publication Data

US 2020/0016373 A1    Jan. 16, 2020

Related U.S. Application Data

(63) Continuation of application No. 12/806,798, filed on Aug. 19, 2010, now Pat. No. 10,463,838.
(Continued)

(51) Int. Cl.
*A61M 25/06* (2006.01)
*A61B 5/00* (2006.01)
(Continued)

(52) U.S. Cl.
CPC ........... *A61M 25/06* (2013.01); *A61B 5/0215* (2013.01); *A61B 5/4839* (2013.01); *A61B 5/489* (2013.01);
(Continued)

(58) Field of Classification Search
CPC .... A61B 5/021; A61B 5/0215; A61B 5/02152
See application file for complete search history.

(56) References Cited

U.S. PATENT DOCUMENTS 3,710,781 A * 1/1973 Huthcins, IV ....... A61B 5/0215
600/488
4,027,669 A   6/1977 Johnston
(Continued)

FOREIGN PATENT DOCUMENTS

CN    1284904    2/2001
CN    1654958    8/2005
(Continued)

OTHER PUBLICATIONS

Merriam-Webster dictionary definition of transrectal (Year: 2024).*
(Continued)

*Primary Examiner* — Jacqueline Cheng
*Assistant Examiner* — Tho Q Tran
(74) *Attorney, Agent, or Firm* — Fitch, Even, Tabin & Flannery LLP

(57) ABSTRACT

A medical device includes a housing having a distal portion with a probe extending therefrom. The housing is graspable by a user to manipulate the housing and the probe. The medical device further includes a pressure sensing system including a pressure sensor and a processing unit coupled with the pressure sensor. The pressure sensor is configured to be carried by the probe. The processing unit is carried by the housing and is configured to receive input signals from the pressure sensor. The medical device further includes an output unit coupled to the processing unit and carried by the housing. The output unit is configured to output a reporting signal to a display. The reporting signal is indicative of a pressure at the pressure sensor.

16 Claims, 23 Drawing Sheets

Related U.S. Application Data

(60) Provisional application No. 61/300,794, filed on Feb. 2, 2010, provisional application No. 61/235,004, filed on Aug. 19, 2009.

(51) Int. Cl.

| | |
|---|---|
| *A61B 5/0215* | (2006.01) |
| *A61B 8/08* | (2006.01) |
| *A61B 17/34* | (2006.01) |
| *A61B 90/00* | (2016.01) |
| *A61M 5/168* | (2006.01) |
| *A61M 5/42* | (2006.01) |
| *A61M 5/46* | (2006.01) |
| *A61B 8/00* | (2006.01) |

(52) U.S. Cl.
CPC ....... *A61B 8/0833* (2013.01); *A61M 5/16854* (2013.01); *A61M 5/427* (2013.01); *A61M 5/46* (2013.01); *A61M 25/0693* (2013.01); *A61B 8/4472* (2013.01); *A61B 17/3401* (2013.01); *A61B 2090/064* (2016.02)

(56) References Cited

U.S. PATENT DOCUMENTS

| | | | |
|---|---|---|---|
| 4,253,850 A | 3/1981 | Rue | |
| 4,364,399 A * | 12/1982 | Dashefsky | A61B 5/4514 600/587 |
| 4,386,606 A | 6/1983 | Tretinyak | |
| 4,428,748 A | 1/1984 | Peyman | |
| 4,648,406 A | 3/1987 | Miller | |
| 4,759,750 A | 7/1988 | Devries | |
| 4,762,533 A | 8/1988 | Oide | |
| 4,801,293 A | 1/1989 | Jackson | |
| 4,848,406 A | 7/1989 | Stauner | |
| 4,907,376 A | 3/1990 | Bouchard | |
| 4,910,924 A | 3/1990 | Bouchard | |
| 4,917,670 A | 4/1990 | Hurley | |
| 4,918,116 A | 4/1990 | Gardziella | |
| 4,994,036 A | 2/1991 | Biscoping | |
| 5,125,898 A | 6/1992 | Kaufhold, Jr. | |
| 5,135,525 A | 8/1992 | Biscoping | |
| 5,141,992 A | 8/1992 | Katoh | |
| 5,171,299 A | 12/1992 | Heitzmann | |
| 5,202,828 A | 4/1993 | Vertelney | |
| 5,205,828 A | 4/1993 | Kedem | |
| 5,215,523 A * | 6/1993 | Williams | G16H 40/63 604/920 |
| 5,267,971 A | 12/1993 | Brimhall | |
| 5,295,967 A | 3/1994 | Rondelet | |
| 5,314,410 A | 5/1994 | Marks | |
| 5,343,868 A * | 9/1994 | Kurscheidt | A61B 5/0215 600/485 |
| 5,445,617 A * | 8/1995 | Yoon | A61B 17/3496 604/164.12 |
| 5,526,820 A | 6/1996 | Khoury | |
| 5,562,609 A | 10/1996 | Brumbach | |
| 5,575,789 A | 11/1996 | Bell | |
| 5,630,802 A | 5/1997 | Moellmann | |
| 5,711,302 A | 1/1998 | Lampropoulos | |
| 5,735,813 A | 4/1998 | Lewis | |
| 5,797,906 A | 8/1998 | Rhum | |
| 5,836,894 A * | 11/1998 | Sarvazyan | A61B 8/12 600/587 |
| 5,865,764 A | 2/1999 | Moorhead | |
| 5,871,470 A | 2/1999 | McWha | |
| 5,902,273 A | 5/1999 | Yang | |
| 5,954,701 A * | 9/1999 | Matalon | A61B 5/1535 604/272 |
| 6,019,775 A | 2/2000 | Sakurai | |
| 6,039,775 A | 3/2000 | Ho | |
| 6,113,574 A | 9/2000 | Spinello | |
| 6,165,142 A | 12/2000 | Bar | |
| 6,190,370 B1 | 2/2001 | Tsui | |
| 6,200,289 B1 | 3/2001 | Hochman | |
| 6,478,769 B1 | 11/2002 | Parker | |
| 6,623,429 B2 | 9/2003 | Percival | |
| 6,673,086 B1 | 1/2004 | Hofmeier | |
| 6,749,496 B2 | 6/2004 | Mota | |
| 6,785,572 B2 | 8/2004 | Yanof | |
| 6,942,561 B2 | 9/2005 | Mota | |
| 7,197,357 B2 | 3/2007 | Istvan | |
| 7,232,430 B2 | 6/2007 | Carlisle | |
| 7,274,956 B2 | 9/2007 | Mott | |
| 7,555,301 B2 | 6/2009 | Skafidas | |
| 7,585,280 B2 | 9/2009 | Wilson | |
| 7,618,409 B2 | 11/2009 | Hochman | |
| 7,896,833 B2 | 3/2011 | Hochman | |
| 7,922,689 B2 | 4/2011 | Lechner | |
| 7,947,001 B1 | 5/2011 | Sarvazyan | |
| 7,955,301 B1 | 6/2011 | Mckay | |
| 8,142,365 B2 | 3/2012 | Miller | |
| 8,282,565 B2 | 10/2012 | Mahapatra | |
| 8,328,738 B2 | 12/2012 | Frankhouser | |
| 8,608,665 B2 * | 12/2013 | Vad | A61B 17/3401 600/587 |
| 8,758,461 B2 | 6/2014 | Yener | |
| 8,814,807 B2 | 8/2014 | Hulvershorn | |
| 8,926,525 B2 | 1/2015 | Hulvershorn | |
| 9,138,867 B2 | 9/2015 | Cai | |
| 9,358,038 B2 | 6/2016 | Hulvershorn | |
| 9,888,881 B2 | 2/2018 | Hulvershorn | |
| 11,607,525 B1 * | 3/2023 | Sutton | A61M 25/0097 |
| 2002/0010390 A1 | 1/2002 | Guice | |
| 2002/0035332 A1 | 3/2002 | Chen | |
| 2002/0042594 A1 | 4/2002 | Lum | |
| 2003/0040737 A1 | 2/2003 | Merril | |
| 2003/0079415 A1 | 5/2003 | Carter | |
| 2003/0097082 A1 | 5/2003 | Purdy | |
| 2003/0199909 A1 | 10/2003 | Boecker | |
| 2004/0010204 A1 | 1/2004 | Weber | |
| 2004/0010251 A1 | 1/2004 | Pitaru | |
| 2004/0024300 A1 | 2/2004 | Graf | |
| 2004/0024358 A1 | 2/2004 | Meythaler | |
| 2004/0098020 A1 | 5/2004 | Nardeo | |
| 2004/0215080 A1 | 10/2004 | Lechner | |
| 2004/0260357 A1 | 12/2004 | Vaughan | |
| 2005/0000455 A1 | 1/2005 | Havermans | |
| 2005/0070458 A1 | 3/2005 | John | |
| 2005/0131345 A1 | 6/2005 | Miller | |
| 2005/0148640 A1 | 7/2005 | Come | |
| 2005/0148940 A1 | 7/2005 | Miller | |
| 2005/0177201 A1 | 8/2005 | Freeman | |
| 2006/0009737 A1 | 1/2006 | Whiting | |
| 2006/0036164 A1 | 2/2006 | Wilson | |
| 2006/0122555 A1 | 6/2006 | Hochman | |
| 2006/0135882 A1 | 6/2006 | Bleich | |
| 2006/0149161 A1 | 7/2006 | Wilson | |
| 2006/0167405 A1 | 7/2006 | King | |
| 2006/0173480 A1 | 8/2006 | Zhang | |
| 2006/0195043 A1 | 8/2006 | Rutherford | |
| 2006/0224223 A1 * | 10/2006 | Podhajsky | A61B 18/148 607/117 |
| 2007/0038129 A1 | 2/2007 | Kishimoto | |
| 2007/0083126 A1 | 4/2007 | Marko | |
| 2007/0088376 A1 | 4/2007 | Zacharias | |
| 2007/0123888 A1 | 5/2007 | Bleich | |
| 2007/0191915 A1 | 8/2007 | Strother | |
| 2007/0239033 A1 | 10/2007 | Tearney | |
| 2007/0255220 A1 | 11/2007 | King | |
| 2007/0265550 A1 | 11/2007 | Choi | |
| 2008/0097287 A1 | 4/2008 | Nelson | |
| 2008/0147094 A1 | 6/2008 | Bittenson | |
| 2008/0154188 A1 | 6/2008 | Hochman | |
| 2008/0182518 A1 | 7/2008 | Lo | |
| 2008/0200789 A1 | 8/2008 | Brister | |
| 2008/0249423 A1 * | 10/2008 | Kitajima | A61B 5/6826 600/500 |
| 2008/0300365 A1 | 12/2008 | Ohtani | |
| 2009/0005675 A1 | 1/2009 | Grunwald | |
| 2009/0005703 A1 | 1/2009 | Fasciano | |
| 2009/0043281 A1 | 2/2009 | Hadzic | |

(56) References Cited

U.S. PATENT DOCUMENTS

| | | |
|---|---|---|
| 2009/0057063 A1 | 3/2009 | Marek |
| 2009/0069709 A1 | 3/2009 | Schmitz |
| 2009/0105554 A1 | 4/2009 | Stahmann |
| 2009/0131832 A1 | 5/2009 | Sacristan Rock |
| 2009/0137952 A1 | 5/2009 | Ramamurthy |
| 2009/0149715 A1 | 6/2009 | Mao |
| 2009/0149771 A1 | 6/2009 | Myklebust |
| 2009/0157044 A1 | 6/2009 | Liyanagama |
| 2009/0171381 A1 | 7/2009 | Schmitz |
| 2009/0204005 A1 | 8/2009 | Keast |
| 2009/0204119 A1 | 8/2009 | Bleich |
| 2009/0240205 A1 | 9/2009 | Wen |
| 2009/0270759 A1 | 10/2009 | Wilson |
| 2009/0275840 A1 | 11/2009 | Roschak |
| 2010/0004558 A1 | 1/2010 | Frankhouser |
| 2010/0069851 A1 | 3/2010 | Vad |
| 2010/0087755 A1 | 4/2010 | Boezaart |
| 2010/0094143 A1 | 4/2010 | Mahapatra |
| 2010/0121270 A1 | 5/2010 | Gunday |
| 2010/0160865 A1 | 6/2010 | Zeltzer |
| 2011/0004159 A1 | 1/2011 | Nelson |
| 2011/0046477 A1 | 2/2011 | Hulvershorn |
| 2011/0054353 A1 | 3/2011 | Hulvershorn |
| 2011/0060229 A1 | 3/2011 | Hulvershorn |
| 2011/0060243 A1 | 3/2011 | Hausman |
| 2011/0077462 A1 | 3/2011 | Saitou |
| 2011/0112362 A1 | 5/2011 | Minetoma |
| 2011/0125107 A1 | 5/2011 | Slocum |
| 2011/0130758 A9 | 6/2011 | Bleich |
| 2011/0155593 A1 | 6/2011 | Zhang |
| 2011/0224623 A1 | 9/2011 | Velez Rivera |
| 2011/0237884 A1 | 9/2011 | Saito |
| 2011/0298628 A1 | 12/2011 | Vad |
| 2012/0216832 A1 | 8/2012 | Pung |
| 2014/0057534 A1 | 2/2014 | Hajduk |
| 2014/0256238 A1 | 9/2014 | Van |
| 2014/0287654 A1 | 9/2014 | Schwabel |

FOREIGN PATENT DOCUMENTS

| | | |
|---|---|---|
| CN | 103370174 | 10/2013 |
| CN | 103406838 A | 11/2013 |
| CN | 104023916 | 9/2014 |
| CN | 104144769 A | 11/2014 |
| EP | 0538259 | 4/1993 |
| FR | 2650957 | 2/1991 |
| GB | 1540511 A | 2/1979 |
| JP | S56104801 | 8/1981 |
| JP | H0686823 | 3/1994 |
| JP | H08507934 | 8/1996 |
| JP | H09232260 A | 9/1997 |
| KR | 20020073824 | 9/2002 |
| KR | 20150014045 A | 2/2015 |
| WO | 9309837 | 5/1993 |
| WO | 1999015315 A1 | 4/1999 |
| WO | 03000146 | 1/2003 |
| WO | 2003086704 A1 | 10/2003 |
| WO | 2007058826 | 5/2007 |
| WO | 2008042625 | 4/2008 |
| WO | 2009023247 | 2/2009 |
| WO | 2009137225 | 11/2009 |
| WO | 2011109188 A2 | 9/2011 |
| WO | 2016154130 | 9/2016 |

OTHER PUBLICATIONS

U.S. Appl. No. 14/268,975, filed May 2, 2014, Hulvershorn Justin.
Don, et al. A Study of Correlation between Epidural and CSF Pressure. The Journal of Korean Society of Anesthesiologists: vol. 23, No. 2, 1990.
European search report and opinion dated Mar. 6, 2014 for EP Application No. 10810289.8.
International search report and written opinion dated Oct. 15, 2010 for PCT /US2010/002305.
Notice of allowance dated Mar. 28, 2014 for U.S. Appl. No. 12/806,809.
Notice of allowance dated May 23, 2014 for U.S. Appl. No. 12/806,747.
Office action dated Jan. 9, 2014 for U.S. Appl. No. 12/806,747.
Office action dated Jan. 23, 2013 for U.S. Appl. No. 12/806,747.
Office action dated Mar. 8, 2013 for U.S. Appl. No. 12/806,809.
Office action dated May 7, 2013 for U.S. Appl. No. 12/806,798.
Office action dated May 17, 2013 for U.S. Appl. No. 12/806,747.
Office action dated Jun. 7, 2012 for U.S. Appl. No. 12/806,747.
Office action dated Sep. 6, 2013 for U.S. Appl. No. 12/806,809.
Office action dated Nov. 6, 2013 for U.S. Appl. No. 12/806,798.
Office action dated Nov. 19, 2012 for U.S. Appl. No. 12/806,798.
Seldinger, Catheter Replacement of the Needle in Percutaneous Arteriography, Presentation at the NAMR, Helsinki, pp. 368-376 ( Year: 1952).
Usubiaga, et al. Effect of Saline Injections on Epidural and Subarachnoid Space Pressures and Relation to Postspinal Anesthesia Headache. Anesthesia and Analgesia Current Researches vol. 46, No. 3, May-Jun. 1976, 293-296.
International Search Report for PCT/US2016/023447, dated Jul. 21, 2016, 1 page.

* cited by examiner

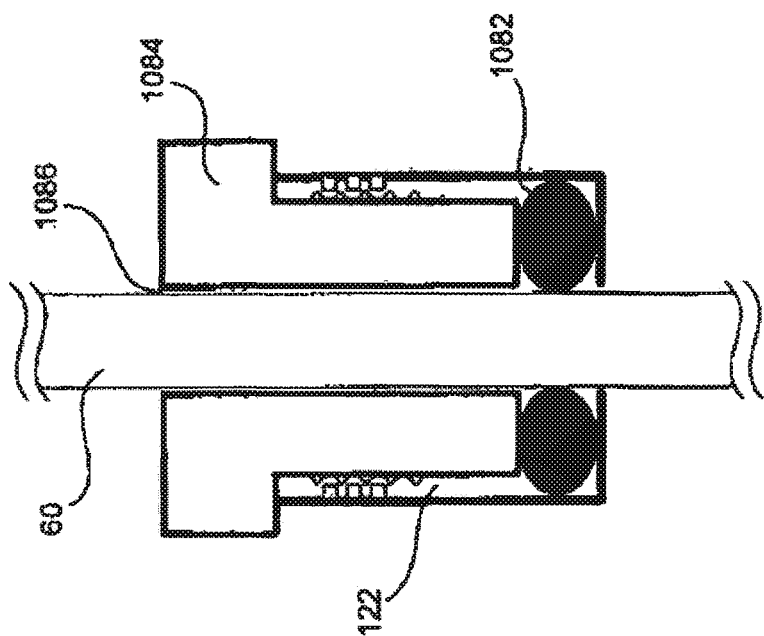
FIG. 2F
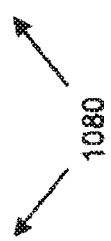
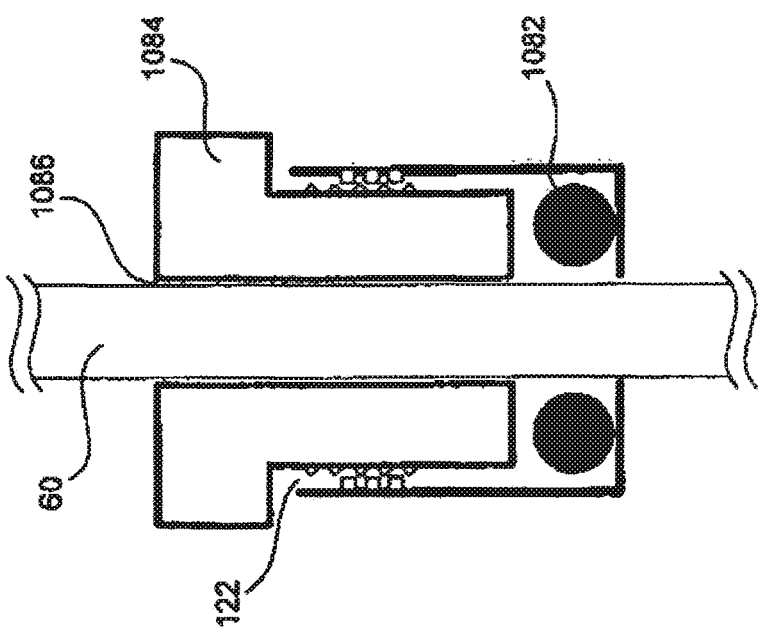
FIG. 2E

| Parameter | Vein | Artery |
|---|---|---|
| Pressure | ≤ 40 mmHG | ≥ 45 mmHG |
| Pressure Variation | ≤ 15 mmHG | ≥ 20 mmHG |
| Hemoglobin Saturation | ≤ 60 % | ≥ 80 % |

FIG. 7

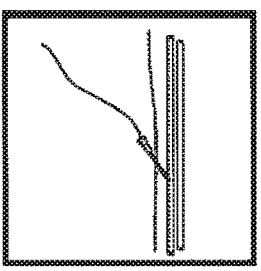
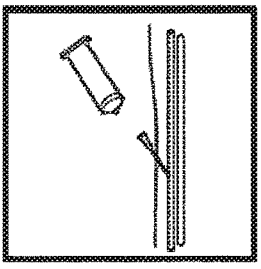
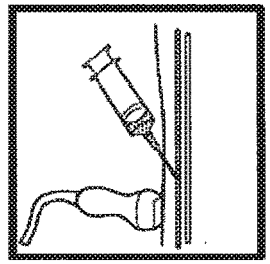
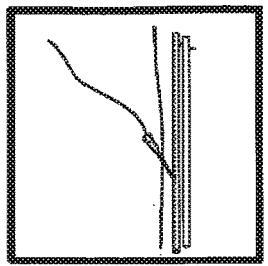
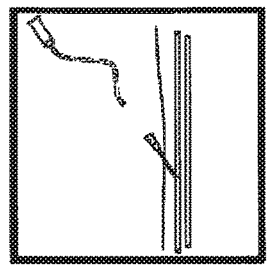
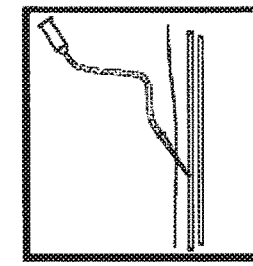
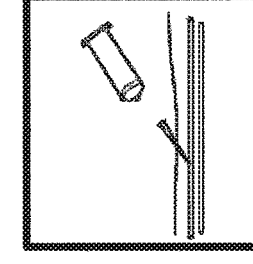
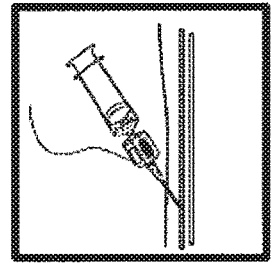
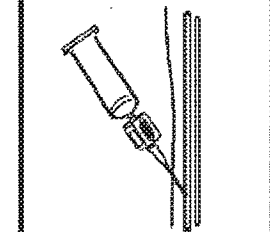

SYSTEMS, METHODS, AND DEVICES FOR FACILITATING ACCESS TO TARGET ANATOMICAL SITES OR ENVIRONMENTS

CROSS-REFERENCE TO RELATED APPLICATION

This application is a continuation from, and claims the benefit under 35 USC § 120 from, U.S. application Ser. No. 12/806,798, filed Aug. 19, 2009, which claims the benefit of priority under 35 U.S.C. § 119 (e) of U.S. Provisional Application No. 61/235,004, filed Aug. 19, 2009, and U.S. Provisional Application No. 61/300,794, filed Feb. 2, 2010, the entire contents of which are incorporated herein by reference. This application is related to U.S. application Ser. No. 12/806,747, now U.S. Pat. No. 8,814,807, filed Aug. 19, 2010, and U.S. application Ser. No. 12/806,809, now U.S. Pat. No. 8,926,525, filed Aug. 19, 2010, the full disclosures of which are incorporated herein by reference.

TECHNICAL FIELD

The present disclosure relates generally to systems, methods, and devices for facilitating access to a target anatomical site. More specifically, aspects of the present disclosure relate to systems, methods and devices that can include one or more sensing units or sensors configured to indicate or verify whether an object, probe, or needle is inserted into a target or a non-target anatomical site, structure, or substance.

BACKGROUND

Needles and catheters are routinely inserted or injected into a patient's body for various purposes or indications. One type of indication that involves such insertion is the placement of vascular lines or catheters, for instance, the placement of a central venous catheter (CVC). A CVC is typically used to administer fluids (e.g., intravenous (IV) drugs, chemotherapeutic agents, blood, or saline) into the body in medical situations in which large fluid transfer volume and/or high fluid transfer rate is desired. Common CVC insertion targets include an internal jugular vein, located in the neck; a subclavian vein, located in the chest; or a femoral vein, located in the groin. A medical procedure known as the Seldinger technique is typically employed for placing CVCs within the body.

The Seldinger technique involves several steps. To establish venous access and CVC insertion via the Seldinger technique, a needle is first placed or inserted into the patient's body at a location expected to correspond to a target vein. A guidewire is then advanced or extended through the needle into the vasculature or vessel in which the needle resides. The needle is subsequently removed while a portion of the guidewire remains retained within the vessel, and a portion of the guidewire remains outside the patient's body. Next, a CVC is advanced over the guidewire into the vessel. Finally, the guidewire is removed, leaving a portion of the CVC within the vessel.

One problem that can arise during CVC placement via the Seldinger technique is a misplacement of either or both of the needle and the CVC. For example, an unintended puncture or tear of a venous wall and/or the placement of one or both of the needle and the CVC into an artery (i.e., an unintended arterial cannulation) can occur, which may result in serious and expensive complications including severe bleeding, emergency vascular surgery, stroke, and possibly death.

Manometry is a technique that has been used for verifying that an appropriate type of blood vessel has been targeted during catheterization (e.g., in association with the Seldinger technique). Conventionally, during manometry directed toward vascular target verification, an extension set (e.g., a 50 centimeter extension tube set) is attached to a needle or a catheter (e.g., an 18-gauge needle or catheter) that has been inserted into a vessel. Blood flows from the patient's body into the needle or catheter, and further flows into an elevated section of tube along the extension set, thereby forming a blood column.

Visible properties of the blood column within the elevated section of tube are assessed by a surgeon or other medical personnel. The assessment of the blood column, for example, a height attained by the blood column, gives an indication as to the pressure of the blood within the vessel under consideration. Such an assessment can enable the surgeon to verify a venous or an arterial placement of the needle or the catheter. However, needle or catheter occlusion or patient state or condition can impact the visible properties of the blood column, and hence the surgeon's assessment, which can lead to a false conclusion about needle or catheter placement. For instance, in a hypotensive patient, an inadvertent arterial needle insertion may not be readily apparent from a naked-eye assessment of blood column height within the elevated section of tube.

Additionally, it has been found that many physicians do not routinely utilize manometry for verifying needle or catheter placement. Furthermore, a needle or a catheter may become dislodged or displaced after performing manometry, which may render its vascular location uncertain. Accordingly, the risk of accidental arterial cannulation during CVC insertion procedures has not been eliminated by the use of manometry. It has also been suggested that the use of manometry may increase the risk of infection or air embolism within the patient.

Ultrasound has been conventionally utilized for determining the position of objects within the body, including needles, guidewires, and catheters. However, images captured with ultrasound may not be adequately informative or clear. For example, ultrasound may be unable to accurately or consistently differentiate between certain tissue types (e.g. between venous tissue and arterial tissue). There have been reported instances of accidental arterial cannulation during CVC placement despite the use of ultrasound. In addition, ultrasound systems or apparatuses belonging to a medical facility are typically shared among multiple groups or departments of that medical facility, and hence may not always be readily available. Additionally, the use of ultrasound for verifying vascular targeting can be time consuming, and thus may be undesirable in critical or emergency situations. Furthermore, the use of ultrasound systems can be comparatively costly and labor intensive.

BRIEF SUMMARY OF THE INVENTION

The present invention provides systems, devices, and related methods for facilitating access to a target anatomical site, which can include detecting or monitoring a physiologic parameter of an anatomical environment in a patient.

In one embodiment, the present invention includes a device for selectively indicating whether an end of a probe inserted into a body is located within a target anatomical environment or a non-target anatomical environment. The device can include a housing detachably couplable to the probe; a chamber carried by the housing; a sensing unit in communication with the chamber, the sensing unit carried by the housing; a processing unit coupled to the sensing unit and carried by the housing, the processing unit configured to determine a first physiologic parameter value using the first set of sensing signals and a second physiologic parameter value using at least one of the first set of sensing signals and the second set of sensing signals, the first and second physiologic parameter values respectively corresponding to a first physiologic parameter and a second physiologic parameter within an anatomical environment; and a set of output devices coupled to the processing unit and carried by the housing, the set of output devices configured to output a set of reporting signals corresponding to at least one of the first physiologic parameter value and the second physiologic parameter value, wherein the second physiologic parameter value differs from the first physiologic parameter value in at least one of a physiologic measurement type and a set of mathematical operations applied to at least one of the first set of sensing signals and the second set of sensing signals.

In another embodiment, a method for determining whether a substance acquired from a body and present within a substance analysis chamber corresponds to a target anatomical location is provided. The method includes establishing at least one from the group of signal communication and substance communication between a set of sensing devices and the substance present within the substance analysis chamber, the set of sensing devices comprising at least a first sensing device, each sensing device within the set of sensing devices operating in accordance with a sensing modality; acquiring a plurality of sensing signals using the set of sensing devices; determining a first physiologic parameter value and a second physiologic parameter value using the plurality of sensing signals, the second physiologic parameter value differing from the first physiologic parameter value in at least one of corresponding to a different sensing device modality and corresponding to a different set of mathematical operations applied to at least one of the first set of sensing signals and the second set of sensing signals; and outputting a set of signals that actively indicates whether the substance corresponds to the target anatomical location.

In yet another embodiment, a device having a processing unit configured to generate an active indication of a probe end positioning at a target anatomical site or an active indication of a probe end positioning at a non-target anatomical site is provided. Such a device can include a housing couplable to a probe; a chamber carried by the housing; a sensing unit in communication with the chamber; a processing unit coupled to the sensing unit and carried by the housing; an electronically programmable medium storing program instructions for causing the processing unit to perform the steps of: determining a first physiologic parameter value using a sensing signal(s); and generating a reporting signal(s) that indicates whether the probe is positioned in the target anatomical location or the non-target anatomical location; and an output device(s) coupled to the processing unit.

In another embodiment, a device for indicating whether an end of a probe inserted into a body is located within a first anatomical environment or a second anatomical environment is provided. The device can include a housing having a first port; a chamber coupled to the first port and carried by the housing; a sensing unit in at least one of signal and substance communication with the chamber, the sensing unit carried by the housing, the sensing unit configured to generate a plurality of sensing signals in accordance with at least one sensing modality; a processing unit coupled to the sensing unit and carried by the housing, the processing unit configured to determine a plurality of physiologic parameter values using the plurality of sensing signals; a set of output devices coupled to the processing unit and carried by the housing, the set of output devices configured to actively output a first set of reporting signals corresponding to the first anatomical environment and configured to actively output a second set of reporting signals corresponding to the second anatomical environment.

In yet another embodiment, the present invention provides a device for detecting whether a distal portion of a probe inserted into a body is located within a target anatomical environment. The device can include a housing having a distal portion with a first port that is detachably couplable to the probe, and a proximal portion with a second port that is detachably couplable to a syringe, and the first port fluidly coupled to the second port; a pressure sensing unit carried by the housing, the sensing unit configured to generate a pressure signal in response to a pressure of an environment in which a coupled probe is positioned; a processing unit coupled to the sensing unit and carried by the housing, the processing unit configured to receive the pressure signal and determine based on the signal a pressure value of the environment about the proximate portion of the coupled probe; and an output unit coupled to the processing unit and carried by the housing, the output unit configured to output to a visual display a reporting signal based on the determined pressure value, wherein the pressure sensing unit, processing unit, and output unit are disposed substantially between the first port and the second port of the housing.

In another embodiment, the present invention includes a device including a housing having a proximal portion and a distal portion with a first port that is detachably couplable to the probe. The device further includes a pressure sensing unit carried by the housing; a processing unit coupled to the sensing unit and carried by the housing; and an output unit coupled to the processing unit and carried by the housing; and a guidewire port carried by the housing and fluidly coupled to the first port.

In yet another embodiment, a device is included, the device having a housing having a distal portion with a first port that is detachably couplable to the probe, and a closed proximal portion; a pressure sensing unit carried by the housing; a processing unit coupled to the sensing unit and carried by the housing; and an output unit coupled to the processing unit and a visual display, and carried by the housing, wherein the visual display is angled proximally as carried by the housing, wherein the pressure sensing unit, processing unit, and output unit are disposed substantially between the first port and the proximal portion of the housing.

The present invention, in yet another embodiment, provides methods for detecting or monitoring a physiologic parameter of a patient. Such a method includes providing a device as described herein, inserting a distal portion of a probe coupled to the device into a tissue or body of a patient, and detecting a physiologic parameter of an environment in which the probe is positioned.

The present invention, according to yet another embodiment, further provides kits or packaged assemblies. A kit can include a device as described herein and one or more probes for coupling to the first port, syringe(s), a guidewire(s), or a catheter(s), or a combination thereof.

For a fuller understanding of the nature and advantages of the present invention, reference should be made to the ensuing detailed description and accompanying drawings.

Other aspects, objects and advantages of the invention will be apparent from the drawings and detailed description that follows.

BRIEF DESCRIPTION OF THE DRAWINGS AND TABLES

FIG. 2E is a cross sectional illustration of a lockable sealing structure in a loose configuration around a guidewire according to an embodiment of the disclosure.

FIG. 2F is a cross sectional illustration of the lockable sealing structure of FIG. 2E in a sealing configuration around a guidewire.

FIG. 7 is a block diagram of a data structure that stores representative data or values corresponding to particular vascular parameters according to an embodiment of the disclosure.

FIGS. 12A through 12D illustrate probe tip location detection under ultrasound guidance.

FIGS. 13A through 13F illustrate probe tip location indication under pressure transduction guidance.

FIGS. 14A through 14C illustrate probe segment or tip indication and guidewire positioning, according to an embodiment of the present invention.

DETAILED DESCRIPTION OF THE INVENTION

Figure 1A:
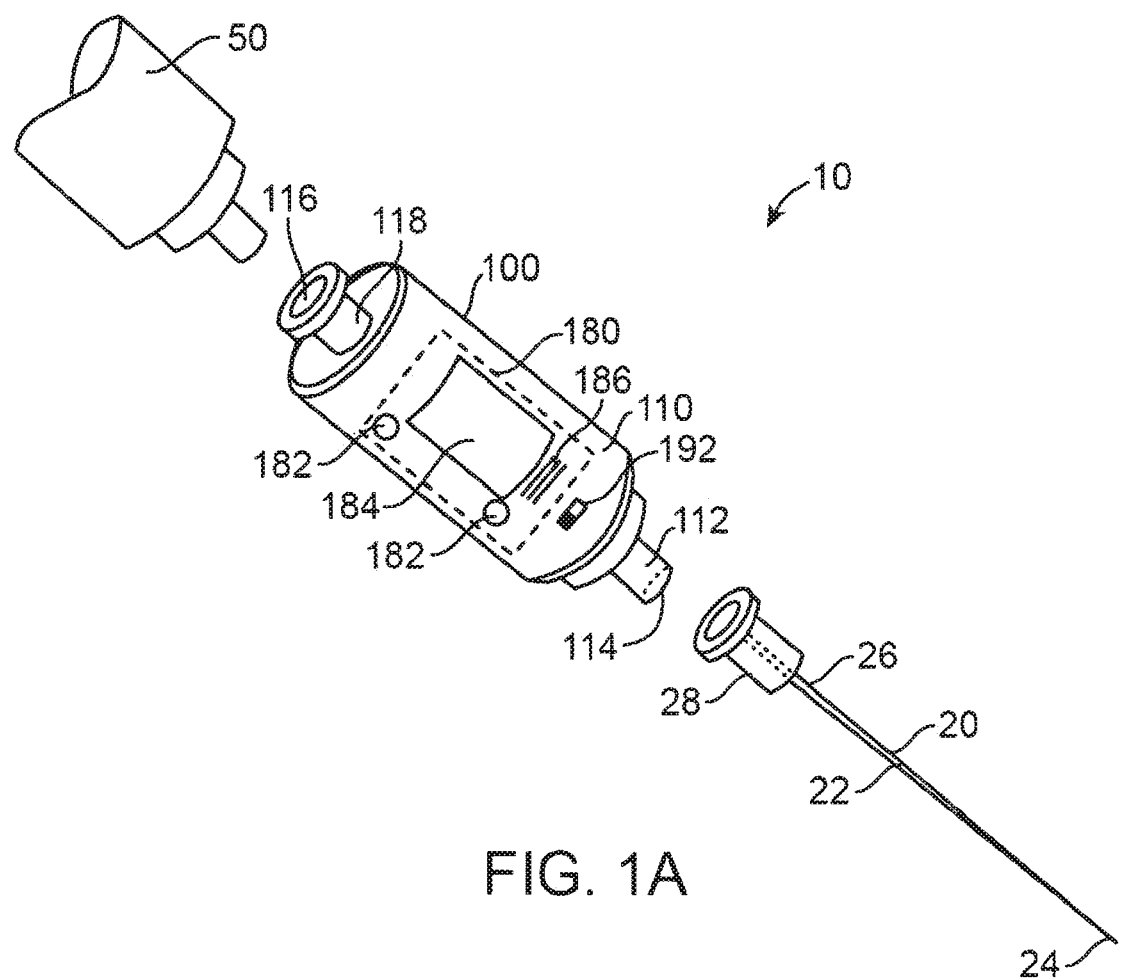
FIG. 1A is a perspective illustration of an apparatus for indicating a probe segment or probe tip location according to an embodiment of the disclosure.

Different types of objects, for example, needles, probes, catheters, tubes, and tissue ablation devices can be inserted into a human or animal body for various medical purposes or indications. Accurate placement or positioning of such objects within the body is generally required. For instance, during venous catheterization, it is important to place a needle or catheter into a target vein or intravenous site, and avoid arterial or non-vascular placement.

Devices of the present invention can be configured for detecting and/or utilizing a single physiological parameter value or a plurality of distinct or different types of physiological parameters. Devices of the present invention that are used for detecting physiological parameters are sometimes referred to herein as detection devices.

Prior approaches fail to provide an active visual indication of whether a probe or needle tip has transitioned into a target anatomical environment as well as an active visual indication of whether the probe or needle tip has transitioned into a non-target anatomical environment, particularly a non-target environment into which device insertion or placement is to be avoided in association with a given medical procedure under consideration (e.g., an arterial site that is to be avoided during a venous access procedure, or vice versa).

Embodiments of the present disclosure are directed to systems, devices, apparatuses, methods, and processes for facilitating, indicating, and/or verifying access to at least one type of target or intended anatomical environment, substance, site, location, structure, tissue, organ, cavity, and/or lumen. Particular embodiments are further directed to systems, devices, apparatus, methods, and processes for indicating or verifying access to at least one type of non-target, unintended, or inadvisable anatomical environment (e.g., in view of a medical procedure directed to the target anatomical environment). Embodiments of the present disclosure can include or involve systems, devices, apparatuses, methods, or processes for detecting, sensing, capturing, measuring, and/or analyzing one or more substances or signals associated with particular physiologic parameters or conditions to facilitate the identification, evaluation, or verification of a location of a portion of an object within a body (e.g., relative to a target or intended anatomical site).

Several embodiments of the disclosure are directed to categorizing or distinguishing between aspects of one or more anatomical substances or sites, for instance, to differentiate or indicate a difference between a first or target anatomical site and a site other than a target anatomical site (e.g., a second or non-target anatomical site); or to determine or indicate whether an anatomical substance originates from or was supplied by, extracted from, or acquired at a first or target anatomical location or structure or a second or non-target anatomical location or structure. Such embodiments can facilitate an automatic or semi-automatic verification or notification that a portion of an object inserted into a body has transitioned into, resides at or within, or has transitioned away from a target substance or site, or one or more non-target substances or sites. Particular embodiments of the disclosure are directed to distinguishing between aspects of an intravascular site and an extravascular site, a venous site and an arterial site, and/or venous blood and arterial blood.

For purposes of brevity and clarity, with respect to various embodiments described herein, an object intended for bodily insertion is referred as a probe that is configured for insertion or injection into biological tissue. Depending upon embodiment details and/or a medical procedure under consideration, a probe can include or be a needle, a catheter, a cannula, a tube, a tissue ablation device, or other type of medical tool or structure. Additionally, a first anatomical environment under consideration may be referred to as a target anatomical environment, and a second anatomical environment under consideration may be referred to as a non-target anatomical environment. Selected embodiments of the disclosure facilitate the determination or indication of whether a segment, end, extremity, point, or tip of a probe or needle resides at a first or target anatomical site or bodily environment; a second or non-target anatomical site or bodily environment; or neither a first/target anatomical site or environment nor a second/non-target anatomical site or environment.

In some embodiments, a target anatomical site or structure is vascular in nature, for instance, a vein or an artery. In such embodiments, a corresponding non-target anatomical site can respectively be an artery or a vein. In other embodiments, a target anatomical site is extravascular or non-vascular in nature. For instance, depending upon embodiment details, a target anatomical site can correspond to a location within a bodily cavity or passage (e.g., the epidural space, the bladder, or the lymphatic system), an organ, a gland, a tissue, or a specified group of cells. A target anatomical substance can be carried by or associated with a target anatomical structure or site. For instance, a target substance such as deoxygenated blood, oxygenated blood, or cerebrospinal fluid can respectively correspond to a target venous, arterial, or subdural site.

A system or apparatus for indicating an anatomical location of a probe or probe tip according to an embodiment of the disclosure can include a probe (e.g., a needle) that is coupled to a housing that carries or couples to one or more devices for detecting, characterizing, evaluating, or analyzing signals and/or substances that can be present at or along a portion of the probe (e.g., at a distal segment or tip of the probe). The system or apparatus includes a set of sensor(s) configured to estimate, detect, record, or monitor a presence, absence, level, or change in one or more physiologic parameters, physiologic parameter correlates, and/or chemical substances corresponding to the probe's insertion path or location at one or more times. In the context of the present disclosure, the term set is defined as a non-empty finite organization of elements that mathematically exhibits a cardinality of at least 1 (i.e., a set as defined herein can correspond to a singlet or single element set, or a multiple element set), in accordance with known mathematical definitions (for instance, in a manner corresponding to that described in An Introduction to Mathematical Reasoning: Numbers, Sets, and Functions, "Chapter 11: Properties of Finite Sets" (e.g., as indicated on p. 140), by Peter J. Eccles, Cambridge University Press (1998)). In general, an element of a set can include or be a device, a structure, a signal, a function or functional process, or a value depending upon the type of set under consideration.

Depending upon embodiment details, representative examples of physiological parameters, physiologic parameter correlates, or chemical substances that can be sensed include one or more of pressure (e.g., intravenous pressure or intraarterial pressure); a pulsatility measure, component, or correlate; temperature; pH; a fluid flow rate; optical properties (e.g., light absorption or scattering properties); oxyhemoglobin or deoxyhemoglobin content or saturation; hemoglobin concentration; tissue oxygen content or saturation; carbon dioxide content or saturation; methemoglobin concentration; nitric oxide content; water content or concentration; electrical properties (e.g., electrical conductivity); a glucose level; a presence or a level of a type of cell (e.g., red blood cells or white blood cells); a presence or level of a pathogen; a presence or level of an immunomodulating factor (e.g, a cytokine), a nutrient or macronutrient (e.g., an amino acid, a protein, a lipid, or a carbohydrate), an enzyme, a hormone, a growth factor, or a genetic marker; a presence or level of a substance such as a drug, a drug metabolite, or a contrast agent; or other another parameter, parameter correlate, or chemical substance.

The presence, absence, relative or absolute level, or change in one or more physiologic parameters, physiologic parameter correlates, or chemical substances can directly or indirectly correspond to an anatomical location or environment at which a portion of the probe resides, and/or a patient state or condition. The system or apparatus may optionally additionally include a processing unit configured to a) generate physiologic parameter values using signals output by the set of sensors; and/or b) analyze or evaluate particular physiologic parameter values. The system or apparatus further includes an output unit configured to generate at least one type of feedback (e.g., audio and/or visual feedback) that indicates whether a portion of the probe under consideration is exposed to or resides at a first or target anatomical site or substance, or a second or non-target anatomical site or substance. In various embodiments, each of the processing unit and the output unit can be carried by the housing, which can be a single use or disposable structure (e.g., a disposable cartridge).

Representative aspects of embodiments of systems, apparatuses, devices, and processes for facilitating access to target anatomical sites or substances in view of particular medical indications or procedures are described in detail hereafter with reference to FIG. 1A to FIG. 9, in which like or analogous elements or process portions are shown numbered with like or analogous reference numerals. Relative to descriptive material corresponding to one or more of FIGS. 1B-9, the recitation of a given reference numeral can indicate the simultaneous consideration of a FIG. in which such reference numeral was previously shown. The description herein provides for embodiments that are suitable for indicating successful or unsuccessful venous or arterial vessel access; embodiments that are suitable for indicating successful or unsuccessful lumbar puncture, epidural space, or cerebrospinal fluid access; and embodiments suitable for other medical indications. The embodiments provided by the present disclosure are not precluded from applications or medical indications (for instance, needle biopsy applications, e.g., involving breast tissue biopsy; or the introduction or injection of polymer-component spheres, or nanospheres or nanostructures into the body) in which particular fundamental principles present among the various embodiments described herein, such as structural, operational, or anatomical site or substance discrimination characteristics, are desired.

Structural and Operational Aspects of
Representative Embodiments

FIG. 1A is a perspective illustration of an apparatus 10 for indicating a probe tip location or environment according to an embodiment of the disclosure. In an embodiment, the apparatus 10 includes a probe site indication device (PSID), probe tip location device (PTLD), or anatomical environment characterization device (AECD) 100 (or detection device) that is coupled to a probe such as a needle 20. The needle 20 includes an elongate member or shaft 22 having a first or insertion end or distal tip 24 and a second or proximal end 26. The needle's shaft is hollow, that is, the needle's elongate member includes a bore that extends between the needle's tip 24 and its proximal end 26. The needle's proximal end 26 can be coupled to a conventional needle coupling or fitting structure 28, such as a Luer adapter, connector, sleeve, collar, or lock. In certain embodiments, the apparatus 10 can further include a syringe 50 that can be coupled to the AECD 100, for instance, by way of a conventional syringe coupling or fitting such as a Luer adapter, connector, sleeve, collar, or lock.

Figure 1B:
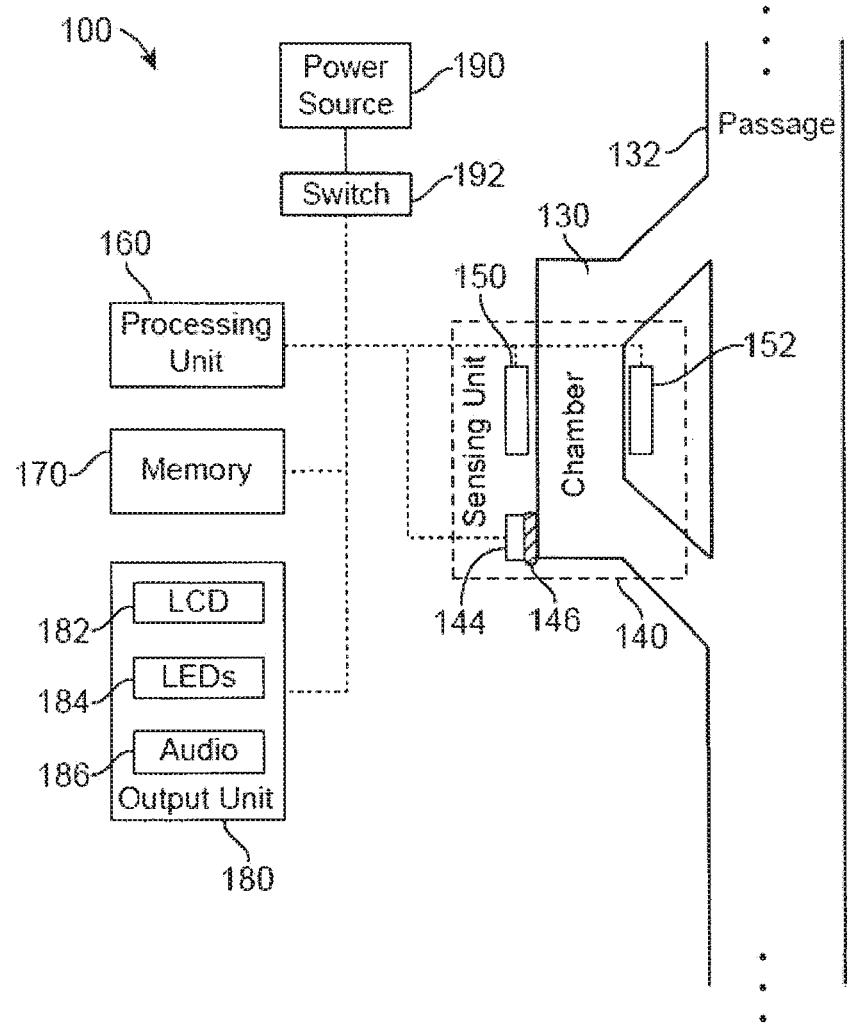
FIG. 1B is a block diagram of an anatomical environment characterization device (AECD) according to an embodiment of the disclosure.

FIG. 1B is a block diagram of an AECD 100 according to an embodiment of the disclosure. With simultaneous reference to FIG. 1A, in various embodiments the AECD 100 includes a housing 110 that carries a first coupling structure 112, a first opening or port 114, at least one fluid or substance detection or analysis chamber or corridor 130 (e.g., a flow-through chamber 130), a sensing unit 140, a processing unit 160, a memory 170, an output unit 180, a power source 190, and an activation switch 192. In some embodiments, the housing 110 can additionally carry a passage 132, a second opening or port 116, and a second coupling structure 118. Each of the sensing unit 140, the processing unit 160, the memory 170, and the output unit 180 are coupled to the power source 190 by way of the switch 192. Selection of a predetermined switch position or a switch toggle can activate the AECD 100. In an embodiment, the power source 190 includes a battery or a capacitor configured to power the AECD 100 for a predetermined or expected total amount of time (e.g., approximately 2 hours, approximately 12 hours, approximately 1 day, or another amount of time).

The first coupling structure 112 carries the first port 114, and includes one or more coupling, fitting, securing, retaining, or connecting elements configured to mate with a given type of probe or needle 20. Similarly, the second coupling structure 118 carries the second port 116, and includes one or more coupling, fitting, securing, retaining, or connecting elements configured to mate with another medical implement such as the syringe 50. One or both of the first and second coupling structures 112, 118 can include or be, for instance, a Luer adapter, taper, collar, slip, connector, or lock structure. For instance, the first coupling structure 112 can include a male Luer lock fitting, and the second coupling structure 118 can include a female Luer lock fitting. In an embodiment, the first and second coupling structures 112, 118 are carried at opposite sides or ends of the housing 110. Each of the first and second coupling structures 112, 118 can carry a removable or pierceable/penetrable end cap or seal (not shown) to facilitate the maintenance of a controlled environment within the AECD 100.

In an embodiment, the chamber 130 includes or forms a cavity or compartment into which a fluid or substance can flow or be drawn, and the passage 132 includes or forms a channel or bore through which the fluid or substance can flow or be drawn. The chamber 130 and the passage 132 are fluid communicable or in fluid communication with the bore of the needle 20 by way of the first port 114. The passage 132 extends between the first port 114 and the second port 116, and hence the second port 116 is fluid communicable or in fluid communication with the bore of the needle 20 by way of the passage 132. Upon insertion or injection of the needle 20 into an individual's body, a bodily fluid such as blood can flow or be drawn from the tip 24 of the needle into the chamber 130 and the passage 132. The bodily fluid can further flow or be drawn through the passage 132 into the syringe 50.

The sensing unit 140 includes a set of sensors, sensing devices, or sensing elements in sensing communication with the chamber 130. More particularly, the sensing unit 140 is in signal and/or substance communication with the chamber 130, such that the set of sensing elements can directly or indirectly apply signals to a substance within the chamber, detect or measure particular properties of a substance present within the chamber, and/or subject a substance within the chamber to one or more tests. Particular sensing elements may detect, measure, or test a property of a substance within the chamber in a manner that avoids direct contact with the substance, while other sensing elements may detect, measure, or test a property of a substance within the chamber by way of direct access to or physical contact with the substance. The chamber 130 can include one or more openings, windows, or ports to facilitate direct access to or physical contact with a substance carried within the chamber 130.

Particular sensors or sensing devices generate sensing signals that correspond to one or more physiologic properties of a substance within the chamber 130 at a particular time. Depending upon the nature or characteristics of a given set of sensing signals, the set of sensing signals may directly provide a value or measure of a physiologic parameter, or the set of sensing signals may be a correlate or partial correlate of the physiologic parameter. If a set of sensing signals provides one or more physiologic parameter correlates or partial correlates, a number of mathematical operations can be applied to at least a subset of signals within the set of sensing signals to generate, determine, or estimate at least one physiologic parameter value.

Any given sensing device operates in accordance with a sensing device modality, which corresponds to a type of signal that the sensing device is configured to acquire and/or a type of physiologic measurement that can be generated or obtained using the sensing signal. A particular sensing device can operate in accordance with a modality such as pressure sensing, optical sensing, temperature sensing, fluid dynamics sensing, chemical or biological species sensing, or another modality. Depending upon embodiment details, the set of sensors or sensing devices can include one or more light emitting diodes (LEDs), semiconductor lasers, optical detectors (e.g., photodiodes, which can be configured to detect optical signal characteristics such as intensity, peak wavelength, or phase shift), pressure sensors (e.g., a diaphragm and/or a pressure transducer such as a piezoelectric transducer), temperature sensors (e.g., an optical temperature sensor or a thermocouple), fluid flow sensors (e.g., a Doppler ultrasound transducer and detector), substance or environment sensing field effect transistors (e.g., a chemical sensing or chemically modified FET (ChemFET), an ion sensitive FET (ISFET), an Enzyme modified FET (EnFET), or an electrolyte-oxide-semiconductor FET (EOSFET)), an electrophoresis device, a biological microchip (e.g., a biochip) or a microfluidic lab-on-a-chip (e.g., as described by Rohit Pal et al. in "An integrated microfluidic device for influenza and other genetic analyses," Lab on a Chip, Royal Society of Chemistry 2005, 5, 1-9), and/or other sensing elements or devices.

In an embodiment directed to indicating venous versus arterial probe access, the set of sensing elements can include one or more devices configured to detect or distinguish between different physiological properties of venous versus arterial blood. More particularly, venous blood and arterial blood exhibit different average pressures, pulse pressure ranges, and blood oxygenation characteristics. In an embodiment, the set of sensing elements can include a pressure sensor and a blood oxygenation sensor. For instance, with respect to sensing pressure related parameters, the set of sensing elements can include a piezoelectric pressure transducer 144 coupled to a diaphragm 146 that is exposed to an opening in the chamber 130. When the chamber 130 is in fluid communication with blood sourced from a vessel, vascular pressure exerts a displacement force upon the diaphragm 146. The diaphragm 146 in turn exerts a force upon the piezoelectric pressure transducer 144, which generates an electrical signal corresponding to an instantaneous, quasi-instantaneous, or near-instantaneous vessel pressure reading at a distal probe segment or the probe tip 24.

In order to sense parameters related to blood oxygenation, the set of sensing elements can include a set of LEDs 150 (e.g., a visible LED and at least one infrared LED) and a photodetector 152. The LEDs 150 are configured to emit optical signals at or centered about particular wavelengths (e.g., approximately 660 nm, and one or more of approximately 905, 910, and 940 nm) into the chamber 130. The photodetector 152 is configured to detect the optical signals that are transmitted through the chamber 130, where optical signal absorption by blood or another substance in the chamber 130 affects the transmitted intensity of such signals. Based upon known oxyhemoglobin and/or deoxyhemoglobin absorbance spectra corresponding to particular optical wavelengths, a blood oxygenation level or state can be determined. The LEDs 150 and the photodetector 152 in this embodiment thus form portions of an oximeter.

The sensing unit 140 is configured to output signals (e.g., sensing signals) to the processing unit 160 and/or the memory 170 on a continuous or periodic basis, and/or in response to one or more sensed parameter values exhibiting a change that exceeds a predetermined magnitude relative to one or more previously sensed parameter values. With respect to the above described embodiment directed to indicating venous versus arterial probe access, the sensing unit 140 can store a series of instantaneous or near-instantaneous pressure values and/or a set of measured optical signal values in the memory 170.

The processing unit 160 can include a state machine, a microcontroller, a microprocessor, an application specific integrated circuit (ASIC), or a field programmable gate array (FPGA) or programmable logic device (PLD) configured to correspond to or execute program instruction sequences (e.g., software and/or firmware) directed to receiving, operating upon, evaluating, analyzing, interpreting, and/or transforming signals generated by one or more portions of the sensing unit 140, and determining whether the tip 24 of the needle 20 resides within a target anatomical site, structure, or substance. In an embodiment, particular program instruction sequences can additionally or alternatively be directed to determining whether the needle tip 24 resides within one or more non-target, undesirable, or inadvisable anatomical sites, structures, or substances. Furthermore, such program instruction sequences can be directed to determining whether the needle tip 24 has transitioned into, resides within, or has transitioned away from one or more intermediary tissues or anatomical environments along a needle insertion trajectory toward a target anatomical destination or environment. In certain embodiments, particular structural portions or operational aspects of the processing unit 160 can be included or incorporated within the sensing unit 140.

In an embodiment, a given type of sensing device operates in accordance with a particular sensing modality and generates a particular type of sensing signal, which depending upon sensing device or sensing signal type can directly or by way of mathematical correlation or transformation provide a physiologic parameter value and hence an indication of a probe tip position. The processing unit 160 can use or mathematically operate upon a set of sensing signals corresponding to a given type of sensing device to determine a single type of physiologic parameter value, or multiple distinct types of physiologic values that differ from each other by way of a set of mathematical operations. For instance, the processing unit 160 can generate a mean value of a physiologic parameter using a time series of sensing signals generated by a given type of sensing device. Additionally or alternatively, the processing unit 160 can additionally or alternatively generate a maximum or mean value of a physiologic parameter fluctuation, range, amplitude, or magnitude using this time series of sensing signals. As a representative example, the processing unit 160 can average a series of sensed instantaneous vascular pressure values to determine a mean vascular pressure value with respect to a predetermined time period (e.g., approximately 1-10 seconds, 30 seconds, 1 minute, or longer). The processing unit 160 can additionally or alternatively determine a maximum and/or average vascular pressure fluctuation value relative to a predetermined time period.

Different types of sensing devices can acquire sensing signals in accordance with different, related, or similar sensing modalities, or generate sensing signals corresponding to different, related, or similar types of physiologic measurements. For example, a pressure sensor generates signals corresponding to pressure measurements, while a chemical species saturation sensor generates signals corresponding to an extent to which the chemical species is dissolved or bound within a bodily substance. As another example, a Doppler ultrasound device and a set of optical emitters/detectors/other optical elements (e.g., configured to perform Doppler or spectroscopic measurements) can each be configured to measure or estimate blood flow, blood flow changes, or pulsatile aspects of vascular flow. In general, the processing unit 160 can mathematically operate upon sensing signals generated by single or multiple types of sensing devices to generate or estimate a given type of physiologic parameter value.

The memory 170 can include an electronically or computer programmable or readable medium having one or more of a Random Access Memory (RAM), a Read Only Memory (ROM) such as a type of programmable ROM (PROM), a set of registers, or other data storage elements for storing a) program instruction sequences; b) signals generated or output by the sensing unit 140 or physiologic parameter values corresponding thereto; and c) reference data that facilitates the determination, evaluation, or analysis of sensed physiologic parameter values. For instance, the memory 170 can store digital absorbance spectra data that a set of program instructions can access to facilitate the evaluation or analysis of sensed blood oxygenation related parameters, and the determination of a blood oxygenation level or state. The memory 170 can also store data (e.g., in a data structure such as a lookup table) that a program instruction sequence can access to a facilitate an assignment or mapping of a set of sensed physiologic parameter values to a categorization of the needle tip's location with respect a target, a non-target, and/or an intermediary anatomical structure or substance, as further detailed below. In association with the execution of one or more program instruction sequences, the processing unit 160 issues or transfers reporting signals to the output unit 180 to facilitate the provision of visual and/or auditory feedback corresponding to the needle tip's sensed location. In various embodiments, the reporting signals can indicate whether the needle tip 24 resides at a first/target anatomical location (e.g., by way of a first set of reporting signals), or a second/non-target anatomical location (e.g., by way of a second set of reporting signals that are perceptually different than the first set of reporting signals), as further detailed below. In one embodiment, the reporting signals can further indicate whether the needle tip 24 resides at neither a first/target anatomical location nor a second/non-target anatomical location (in which case the needle tip 24 may reside at an anatomical location that is unrelated to the first/target anatomical location and the second/non-target anatomical location). Particular aspects of processes that can correspond to an automated sequence (e.g., performed by way of program instruction execution) directed to presenting physiologic parameter values to a user (e.g., a surgeon or other medical professional) or observer and/or indicating a position of a probe segment or tip 24 relative to a target, non-target, and/or intermediary anatomical site or structure are described in detail below with reference to FIGS. 8-9.

In response to the reporting signals, the output unit 180 is configured to generate and actively provide or convey visual and/or auditory signals that can indicate (e.g., in a selective manner) whether the needle tip 24 resides at or within a target or non-target anatomical site, structure or substance. In an embodiment, the output unit 180 actively provides or conveys a visual and/or auditory indication of a needle tip location by applying a non-zero amount of power to an output device, thereby activating the output device to selectively emit, radiate, or externally propagate a) a first signal that provides a user or observer with sensory feedback (visual and/or auditory feedback) that can indicate whether the needle tip 24 resides at a first or target anatomical site; and b) a second signal that provides the user or observer with sensory feedback that can indicate whether the needle tip 24 resides at a second or non-target anatomical site. In one embodiment, in the event that the processing unit 160 determines that the needle tip 24 resides at neither of a first/target anatomical location or a second/non-target anatomical location, the output unit 180 can be configured to avoid actively outputting visual and/or auditory signals. Alternatively, the output unit 180 can be configured to actively output a third signal that provides a user or observer with sensory feedback that can indicate a neutral or intermediary needle tip location.

Depending upon embodiment details, the reporting signals can correspond to notification signals and/or alert signals. Notification signals can indicate or provide one or more detected, measured, or estimated physiological parameter values corresponding to sensing unit operation. Notification signals can include, for instance, visual and/or auditory signals corresponding to one or more physiologic parameter values such as a blood oxygen saturation level, a blood pressure value, and/or a pulsatility measure or a peak-to-minimum blood pressure difference value. Alert signals can include visual and/or auditory signals that provide a binary or "yes/no" indication or a likelihood indication (e.g., a probability based indication, as determined in association with the execution of a program instruction sequence) of an intended or appropriate probe or needle positioning. In an embodiment, alert signals can further provide a binary or "yes/no" indication or a likelihood indication of an unintended, undesirable, or incorrect probe positioning.

The output unit 180 can output multiple reporting signals in a simultaneous or non-simultaneous (e.g., sequential) manner. Notification or alert signals can be presented on an essentially continuous, sampled, or periodic basis following AECD activation, or in response to a trigger event such as a first detection of one or more physiologic parameter values that correspond to a target or a non-target anatomical needle tip placement, or a predetermined change in a physiologic parameter value.

In general, the output unit 180 can include one or more types of output devices, for instance, a liquid crystal display (LCD) 182, a set of LEDs 184, and possibly an audio device such as a speaker 186. In an embodiment, notification signals displayed by the LCD 182 (e.g., on a real-time, near real-time, a periodic basis, or in response to a given amount of physiologic parameter change) can include or correspond to particular physiologic parameter values, for instance, a hemoglobin oxygen saturation value, a blood pressure value, and/or a pulsatility value. The presentation of particular physiologic parameter values to a user or observer can facilitate the determination or confirmation of a probe tip location relative to a target or non-target anatomical site. In addition or as an alternative to the foregoing, the LCD 182 can display textual alert signals such as "venous access detected" and/or "warning-arterial access detected," where the visual impact of one or both of such alert signals may be enhanced by way of a visual effect such as flashing.

The set of LEDs 184 can include a first LED 184*a* that is activated or illuminated when or while one or more sensed, estimated, or measured physiologic parameter values indicate that the needle tip 24 resides within a target site (e.g., a vein); and a second LED 184*b* that is activated or illuminated when or while one or more sensed, estimated, or measured physiologic parameter values indicate that the needle tip 24 resides within a non-target site (e.g., an artery). For an apparatus 10 directed to indicating or confirming successful venous access and providing an alert in the event of arterial access, the first LED 184*a* can output light substantially having a first color (e.g., blue or green) and possibly a first activation pattern (e.g., continuous illumination); and the second LED 184*b* can output light substantially having a second color (e.g., red, or another color that is visually distinguishable from the first color) and possibly a second activation pattern (e.g., blinking).

Finally, the speaker 186 can output a first audio alert signal such as a tone or digital voice signal that indicates whether the needle tip 24 is positioned at or within a target anatomical site. In an embodiment, the speaker 186 can additionally output a second audio alert signal that indicates whether the needle tip 24 is positioned at or within a non-target anatomical site. In a representative implementation directed to facilitating venous access and avoiding arterial access, the first audio signal can include a digitized voice signal that corresponds to a phrase such as "venous access detected," and the second audio signal can include a digitized voice signal that corresponds to a phrase such as "warning-arterial access detected." In another embodiment, the speaker 186 can output one or more audio notification signals that correspond to or indicate the values of sensed, estimated, or measured physiologic parameters (for instance, the speaker 186 can output audio signals corresponding to internal bodily sounds, pressure waves, or pressure changes).

In view of the foregoing, in an embodiment the apparatus 10 can differentially communicate or convey by way of output device activation one or more indications of probe tip or distal segment position relative to a target and/or a set of non-target anatomical sites, structures, or substances. In such an embodiment, the output unit 180 can include a) at least one output device capable of providing at least a two-state active indication of reporting signal values or probe tip positions with respect to the target and non-target anatomical sites; or b) multiple output devices, each of which is capable of providing at least a single-state active indication of a reporting signal value or a probe tip position with respect to the target or non-target anatomical sites.

In a representative embodiment, a display device can provide a two-state active indication of two reporting signal values by way of two displayed values. An audio device can provide a two-state active indication of two reporting signal values by way of two types of audio tones or messages. Additionally, a multi-color LED or a multi-color LED array can provide a two-state active indication of two reporting signal values by way of outputting light of different colors that can be readily distinguished by the human eye.

Figure 1C:
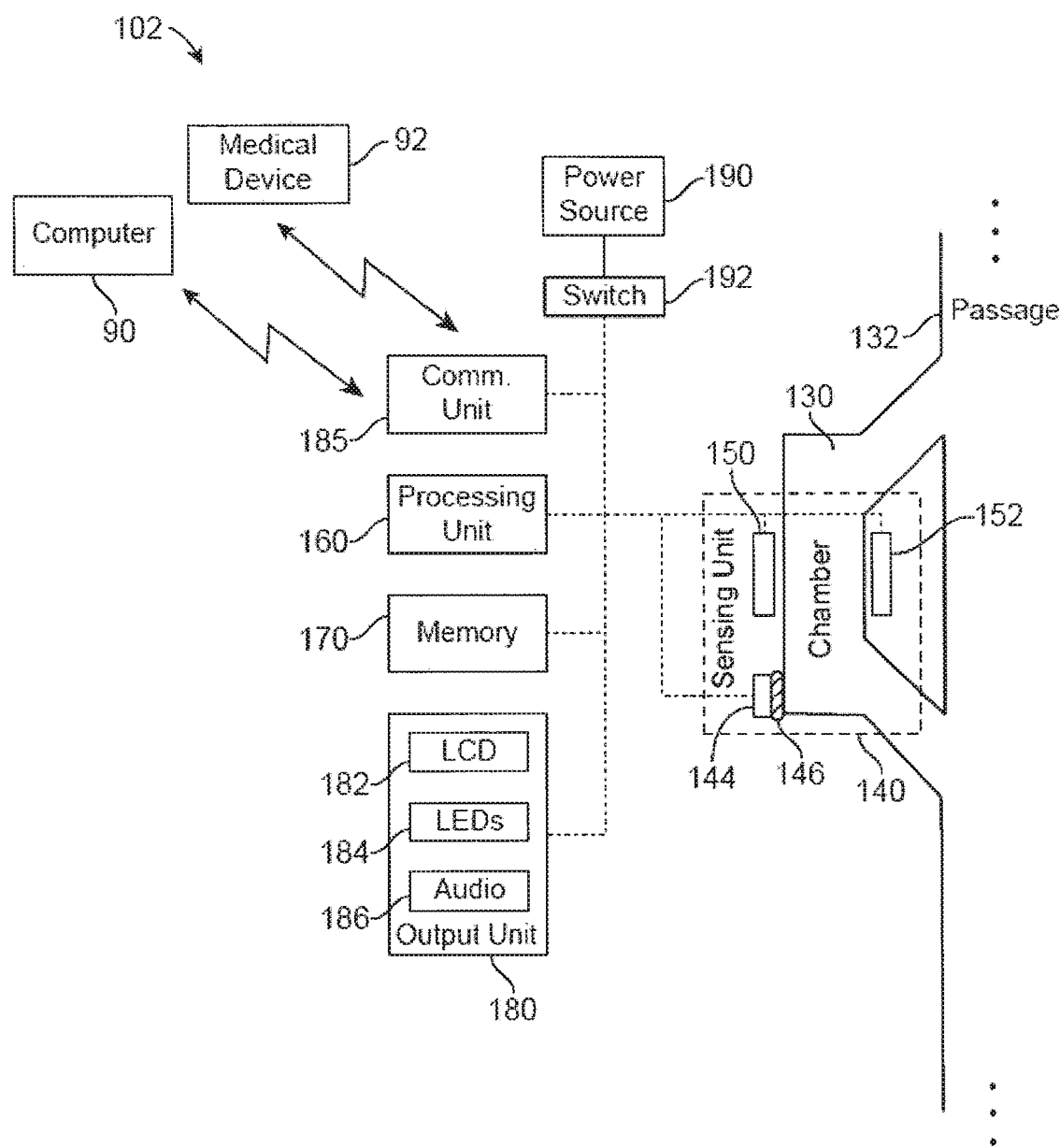
FIG. 1C is a block diagram of a device according to another embodiment of the disclosure.

FIG. 1C is a block diagram of an AECD 102 according to another embodiment of the disclosure, in which the AECD 102 is configured to communicate with a remote or external device such as a computer system 90 (e.g., a desktop computer, a laptop computer, or a personal digital assistant) or a given piece of medical equipment 92. In the embodiment shown, in addition to including the elements described above with respect to FIG. 1B, the AECD 102 includes a communication unit 185 that is coupled to the memory 170, the processing unit 180, and the switch 192, which selectively couples the AECD 102 to the power source 190. The communication unit 185 can further be coupled to the sensing unit 140. The communication unit 185 can be configured for wireless or wire-based signal transfer involving the remote computer system 90 or medical device 92, such as an ultrasound system or device (e.g., portable ultrasound unit), and the like. In a representative implementation, the communication unit 185 includes a radio frequency (RF) communication circuit.

Thus, in certain embodiments, a sensing device of the present invention, including those described herein, may be operable in communication with another separate or remote device, including output of data to the remote device, uploading or receiving data from the remote device, or both outputting and receiving data. Output of data from a device of the present invention to a remote device may be selected, for example, for visual display of data from the sensing device on the remote device display or screen. Data from a remote device may, in certain instances, be received by a sensing device of the present invention, and data from the remote device optionally being displayed on the sensing device.

By way of the communication unit 185, the AECD 102 can transfer a sequence of physiologic or physiologic correlate parameter values to one or more remote systems or devices 90, 92. Additionally or alternatively, the communication unit 185 can transfer reporting signals or notification and/or alert signals to a remote system or device 90, 92. One or more of physiologic or physiologic correlate parameter values, reporting signals, notification signals, and alert signals can reside in the memory 170 to facilitate such transfer. Signal transfer between the AECD 102 and a remote system or device 90, 92 can occur on a real time, near-real time, periodic, event triggered, or command-response basis while the AECD 102 is active. In an embodiment, signal transfer to a remote system or device 90, 92 can be initiated or triggered in response to the detection (e.g., optical detection) of blood or another bodily fluid in the chamber 130. Additionally or alternatively, signal transfer from the AECD 102 to the remote system or device 90, 92 can include a medical procedure data upload process involving the transfer of physiologic or physiologic correlate parameter values, reporting signals, notification signals, and/or alert signals that the sensing and/or processing units 140, 160 had stored or recorded in the memory 170 during or throughout one or more time intervals corresponding to a medical procedure (e.g., during a 15 or a 30 minute period following AECD activation/chamber fluid detection in association with a CVC placement procedure). Furthermore, in an embodiment the communication unit 185 can download or receive AECD configuration data or program instruction sets from a remote computer system 90 to the memory 170, such that the AECD 102 can be programmably reconfigured (e.g., by way of a transfer of a firmware update, a program instruction sequence, or a programmable logic configuration bitstream) on an as-needed basis (e.g., in view of a given medical indication).

In an embodiment, the sensing unit 140 and/or the processing unit 160 can store or record measured or sampled pressure and/or other physiologic parameter values in the memory 170 on an essentially continuous or sampled basis (e.g., approximately every 0.5-500 milliseconds, or approximately every 2.5-250 milliseconds, or approximately every 5, 10, 50, or 100 milliseconds) or at predetermined time intervals. The communication unit 185 can transfer stored pressure values to a remote device 92 that is configured to receive the individual pressure values and display and/or analyze a corresponding pressure waveform (e.g., a vascular pressure waveform). Such transfer can occur on an essentially real time or near-real time basis, or a delayed basis.

Figure 2A:
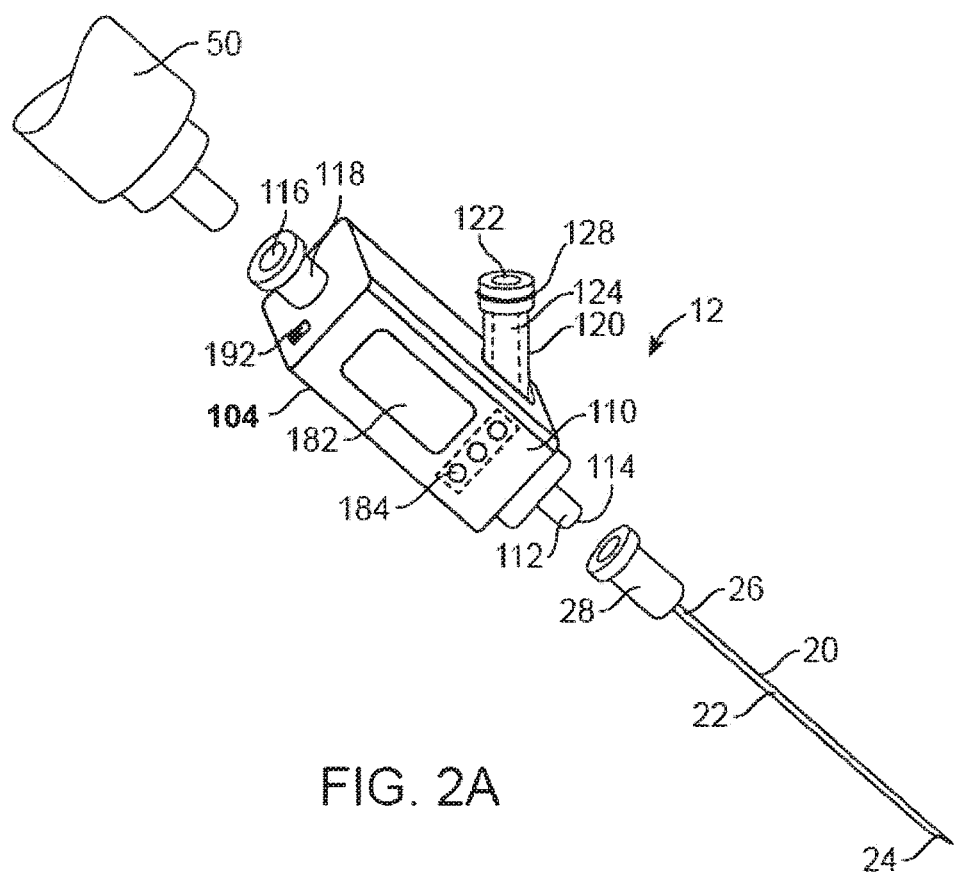
FIG. 2A is a perspective illustration of an apparatus for indicating a probe segment or probe tip location according to another embodiment of the disclosure.

FIG. 2A is a perspective illustration of an apparatus 12 for indicating a probe segment or probe tip location according to another embodiment of the disclosure. In an embodiment, the apparatus includes a probe or needle 20 that is coupled to an AECD 104 having at least one auxiliary, adjunctive, subsidiary, or supplementary access structure, member, or shaft 120. The auxiliary access structure 120 includes an auxiliary access port 122 configured for fluid communication with the AECD's passage 132. In an embodiment, the auxiliary access port 122 resides at a distal portion or end of a channel 124 carried by the auxiliary access structure 120. A proximal portion or end of the channel 124 is coupled to the AECD's passage 132 by way of an opening, such that the auxiliary access port 122 is fluid communicable or in fluid communication with the passage 132. The auxiliary access structure 120 can extend at a predetermined angle (e.g., approximately 45 degrees) away from a surface or side of the AECD 104. In general, the auxiliary access structure 120 is offset from an AECD surface or side that carries the output unit 180.

The auxiliary access port 122 facilitates the insertion of one or more types of auxiliary or adjunctive devices into the passage 132 of the AECD 104, and possibly through the AECD 104 and into or through the bore of the needle 20. An auxiliary device can include, for instance, a guidewire 60 or a sensing device that carries a set of sensing elements configured for insertion into a patient's body. The auxiliary access structure 120 can carry a removable or pierceable/penetrable end cap or seal (not shown) that prevents the exposure of a fluid present within the AECD 104 to an external environment until the seal is removed or pierced. Additionally, the auxiliary access structure 120 can include a set of dynamic sealing elements 128 such as one or more o-rings (e.g., located or seated at a distal segment or end of the auxiliary access structure 120) that facilitate the maintenance of a leak proof or leak resistant seal around the periphery of an auxiliary access device after auxiliary access device insertion. The presence of a dynamic sealing element 128 can ensure that sensed blood pressure values remain accurate or consistent after an auxiliary access device such as a guidewire 60 resides within a portion of the AECD 104.

Depending upon embodiment details, the auxiliary access structure 120 can carry or include one or more types of structural elements that facilitate the maintenance of pressure integrity within the AECD 104 following insertion of a guidewire or other device (e.g., a set of optical fibers) into the auxiliary access port 122 and the auxiliary access structure's channel 124. Particular types of structural elements that facilitate the maintenance of a seal around a guidewire or other device are described in detail hereafter.

Figure 2B:
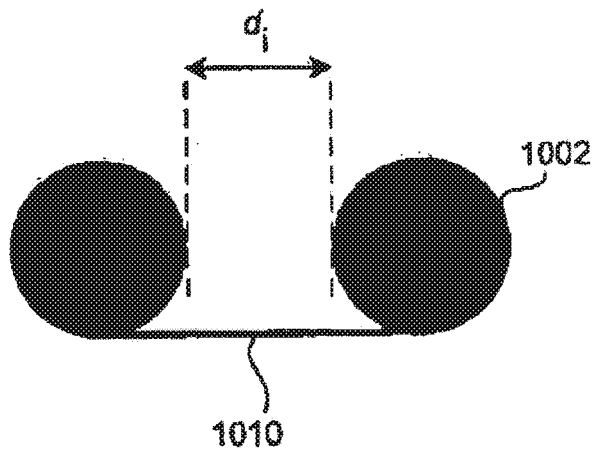
FIG. 2B is a cross sectional illustration of a webbed o-ring structure according to an embodiment of the disclosure.
Figure 2C:
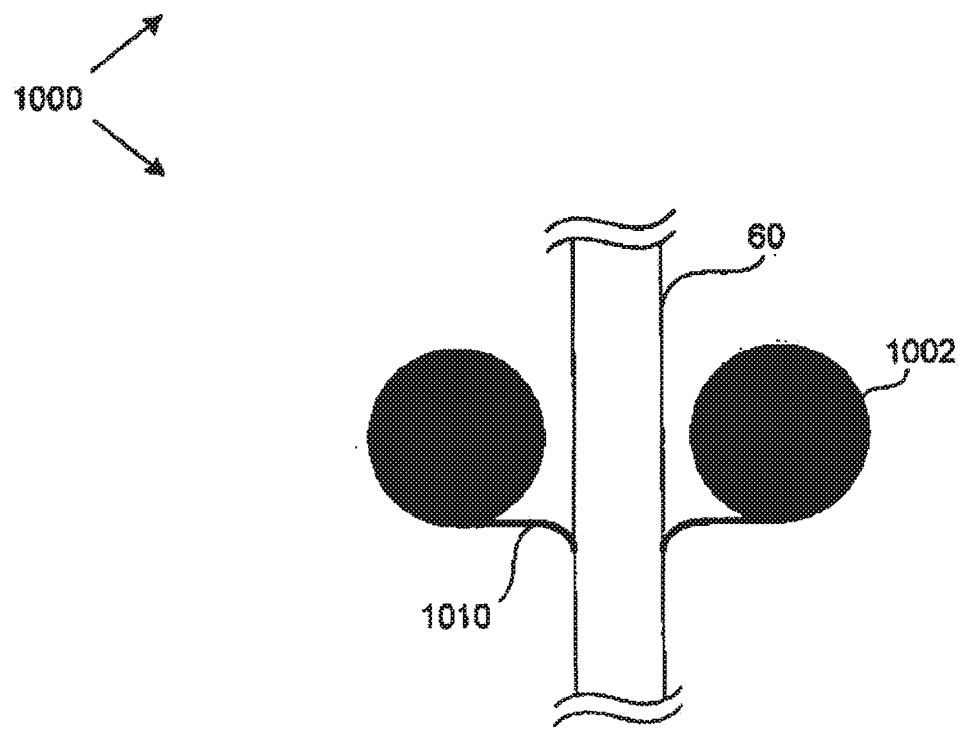
FIG. 2C is a cross sectional illustration of the webbed o-ring structure of FIG. 2B in a sealing configuration around a guidewire.

FIG. 2B is a cross sectional illustration of a webbed o-ring structure 1000, and FIG. 2C is a cross sectional illustration of the webbed o-ring structure 1000 in a sealing configuration around a guidewire 60 according to an embodiment of the disclosure. In an embodiment, the webbed o-ring structure 1000 includes an o-ring 1002 that carries a resilient, pierceable web or membrane 1010 that spans an inner diameter di of the o-ring 1002. Upon guidewire insertion through the membrane 1010, a portion of the membrane 1010 surrounding the guidewire 60 dynamically conforms to the guidewire's periphery, thereby establishing a continuous seal between the guidewire 60 and the membrane 1010. In a representative implementation, each of the o-ring and the membrane 1010 can be made using Silicone.

Figure 2D:
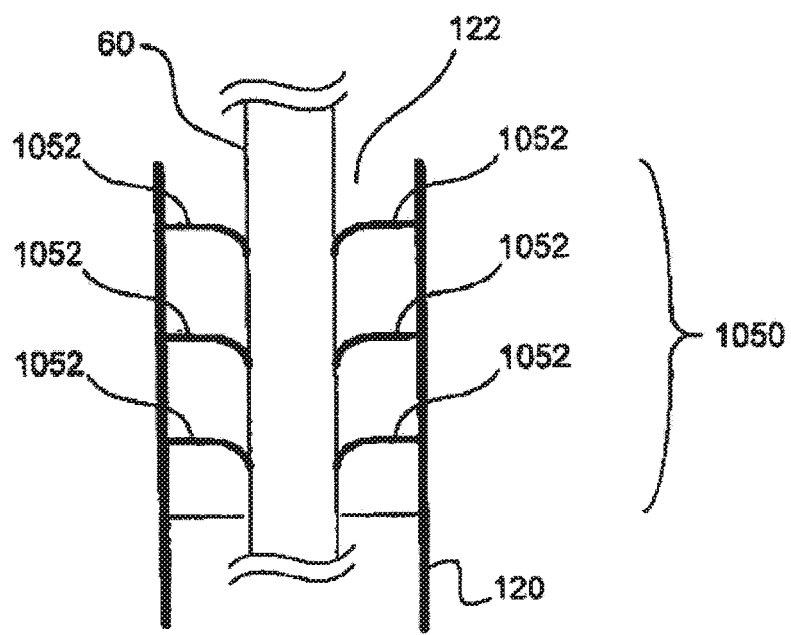
FIG. 2D is a cross sectional illustration of a flexible seal structure according to an embodiment of the disclosure.

FIG. 2D is a cross sectional illustration of a flexible seal structure 1050 according to an embodiment of the disclosure. In an embodiment, the flexible seal structure 1050 includes a plurality of pierceable seal elements 1052 carried at, proximate to, or along an insertion end of the auxiliary access structure 120. Each seal element 1052 comprises a pierceable and resilient or flexible material, which can include for instance, Silicone. On an individual basis, upon guidewire insertion, a portion of each any given seal element 1052 surrounding the guidewire 60 dynamically conforms to the guidewire's periphery. Thus, following guidewire insertion through the plurality of seal elements 1052, the plurality of seal elements 1052 form a composite seal that facilitates the maintenance of intra-AECD environmental integrity.

FIG. 2E is a cross sectional illustration of a securable or lockable sealing structure 1080 in a loose configuration around a guidewire 60, and FIG. 2F is a cross sectional illustration of a lockable sealing structure 1080 in a sealing configuration around a guidewire 60 according to an embodiment of the disclosure. In an embodiment, the lockable sealing structure 1080 includes an o-ring 1082 carried by a portion of the auxiliary access structure 120 proximate to the auxiliary access port, and a knob 1084 that matingly fits into the auxiliary access port 122. The knob 1084 includes an opening or channel 1086 therethrough, which is dimensioned to accommodate the periphery of a guidewire 60 or other device.

An external portion of the knob 1084 and an internal portion of the auxiliary access port 122 can carry counterpart thread elements that facilitate screw-type insertion and selectable locking (e.g., by hand or use of a knob adjustment tool) of the knob 1084 in the auxiliary access port 122. When the knob 1084 remains in a first or unlocked position, the o-ring 1082 is uncompressed. A guidewire 60 extending through the knob's channel 1086 can therefore slidably move into and along the length of the auxiliary access structure's channel 124 with minimal, negligible, or no friction resulting from o-ring contact with the guidewire 60. Turning the knob 1084 to a second or locked position compresses the o-ring 1082, thereby decreasing the o-ring's inner diameter such that the o-ring 1082 abuts and surrounds the periphery of the guidewire 60 and forms a seal around the guidewire 60. Transitioning the knob 1084 to a locked position can correspondingly lock the guidewire 60 in place.

Figure 2G:
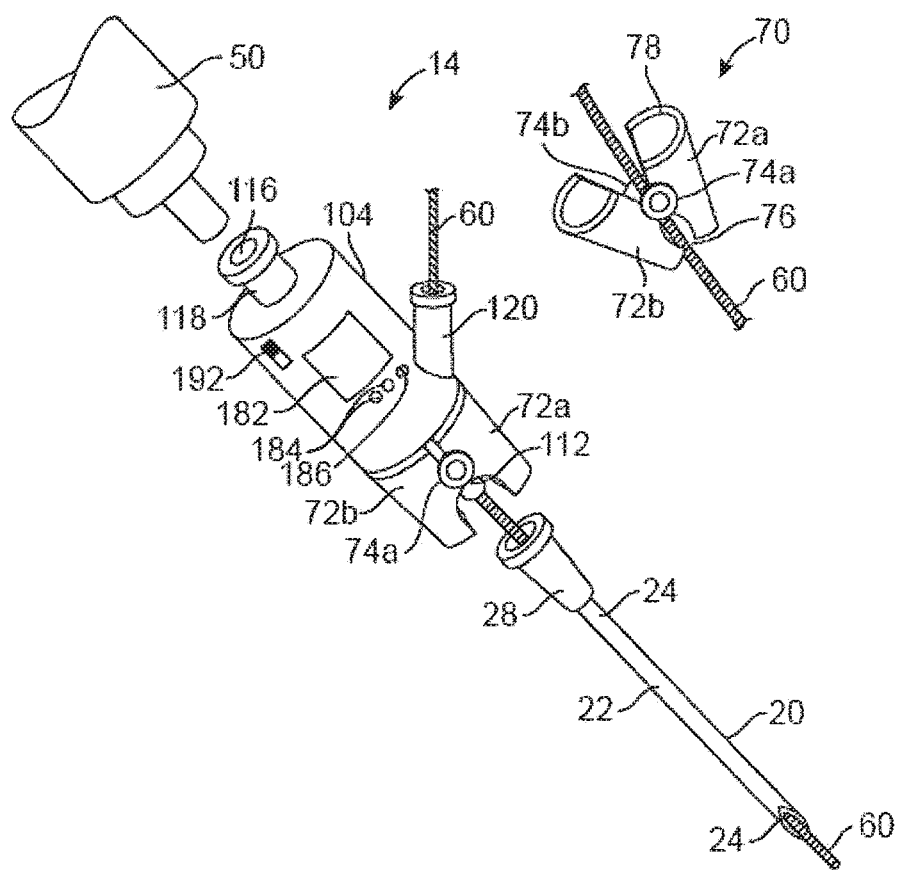
FIG. 2G is a perspective illustration of an apparatus for indicating a probe segment of probe tip location according to a further embodiment of the disclosure.

FIG. 2G is a perspective illustration of an apparatus 14 for indicating a probe segment or probe tip location according to a further embodiment of the disclosure. The apparatus 14 includes a probe or needle 20; an AECD 104 having an auxiliary access port 122; and possibly a syringe 50. In an embodiment, the apparatus 14 additionally includes a guidewire 60 and a guidewire retention device 70. In general, the guidewire retention device 70 includes a set of receiving structures that can releasably carry portions of the AECD 104, and which can restrain, grasp, capture, or clamp the guidewire 60 following AECD removal from the guidewire retention device 70, as further detailed below. The guidewire retention device 70 facilitates the withdrawal of the AECD 104 and the needle 20 from the guidewire 60 as an integral unit or separate units in association with the capture of the guidewire 60 at or along a given portion of the guidewire's length.

The guidewire retention device 70 can include a first receiving portion 72 *a* and a second receiving portion 72 *b* that are pivotally coupled at or about a first and a second hinge point by a first and a second hinge member 74 *a*, 74 *b*, respectively, one or both of which are resiliently releasable and/or positionally lockable. The guidewire retention device 70 includes a capture end 76 and a receiving end 78. In an embodiment, one or both hinge members 74 *a*, 74 *b* can include a biasing element such as a spring that maintains the guidewire retention device 70 in a capture position in which the first and second receiving portions 72 *a*, 72 *b* are retained in close or generally close proximity to each other at the guidewire retention device's capture end 76, such that a separation or gap between the first and second receiving portions 72 *a*, 72 *b* is slightly less than the diameter of the guidewire 60.

The AECD 104 can be inserted into the guidewire retention device's receiving end 78, and the first and second receiving portions 72 *a*, 72 *b* can be positioned or secured around portions of the AECD's periphery, thereby maintaining the guidewire retention device 70 in a carry position. One or both of the first and second receiving portions 72 *a*, 72 *b* can include a contoured inner surface that facilitates the automatic or semi-automatic closure of the first and/or second receiving portions 72 *a*, 72 *b* around a portion of the AECD's periphery in response to insertion of the AECD 104 into the guidewire retention device 70. While in the carry position, the first and second receiving portions 72 *a*, 72 *b* are separated from each other at the guidewire retention device's a) receiving end 78 by a distance corresponding to the external or exterior profile of the AECD 104; and b) capture end 76 by a distance that exceeds the diameter of the guidewire 60 and which facilitates unhindered or generally unobstructed coupling of the needle 20 to the AECD's first coupling structure 112.

In association with a representative medical procedure, the guidewire retention device 70 can initially hold or carry the AECD 104, and the needle's coupling structure 28 can be fitted to the AECD's first coupling structure 112. Following the injection of the needle 20 into a patient's body and a determination that the tip 24 of the needle 20 resides at or within a target anatomical location (e.g., a vascular structure such as the left internal jugular vein) in accordance with an embodiment of the disclosure, a guidewire 60 can be inserted into and through the AECD 104 and the needle 20, such that a portion of the guidewire resides at or within the target anatomical location. The AECD 104 and the needle 20 can subsequently be withdrawn from the guidewire 60, for instance, by a force that pulls the AECD 104 and the needle 20 away from the patient's body while the guidewire retention device 70 is held in a stationary or generally stationary position. Upon removal of the AECD 104 and the needle 20 from the guidewire retention device 70, the guidewire retention device 70 can resiliently or automatically transition to the retaining position, such that the first and second receiving portions 72 a, 72 b grasp or restrain the guidewire 60 at the guidewire retention device's capture end 76.

Figure 3:
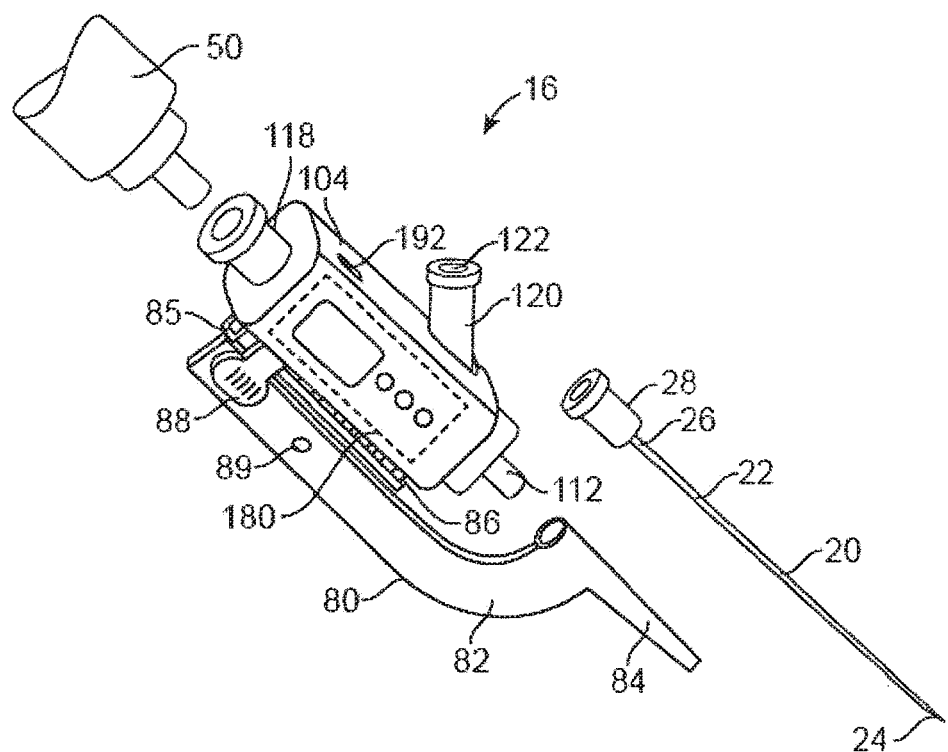
FIG. 3 is a perspective illustration of an apparatus for indicating a probe segment or probe tip location according to another embodiment of the disclosure.

FIG. 3 is a perspective illustration of an apparatus 16 for indicating a probe segment or probe tip location according to another embodiment of the disclosure. In an embodiment, the apparatus 16 includes a probe or needle 20; an AECD 104, which may have an auxiliary access port 122; and possibly a syringe 50. In an embodiment, the apparatus 14 additionally includes a movable or repositionable dilator or dilator assembly 80 that is coupled to the AECD 104, and which in a particular embodiment is coupled to the AECD 104 in a removable, releasable, or detachable manner. In general, the repositionable dilator 80 includes a support arm 82 that carries a dilating member 84, a first positioning member 85, and a release element 88. The AECD 104 can carry a second positioning member 86 that matingly fits into or receives the first positioning member 85 in a manner that facilitates adjustable or slidable movement of the dilator 80 relative to the AECD 104 along a direction or axis that is parallel to the bore of the needle 20. In a representative implementation, the first positioning member 85 can include a receiving structure having a groove or slot, and the second positioning member 86 can include a spine configured for insertion into the slot and progressive displacement along the slot's length. The dilator 80 can additionally carry a position control element 89 such as a lever or knob.

The dilating member 84 includes a tapered hollow enclosure having a predetermined largest diameter at a proximal end, a predetermined smallest diameter at a distal end, and a progressive diameter taper between its proximal end and distal end. The predetermined smallest diameter is slightly larger than the diameter of the needle. The dilator 80 can receive the AECD 104 and the needle 20 as an integral unit. More particularly, the AECD 104 and a needle 20 coupled thereto can be mounted to the dilator 80 such that the first positioning member 85 resides along a portion of a side or surface of the AECD 104 that carries the second positioning member 86, and the dilating member 84 surrounds a portion of the needle's shaft 22.

The position control element 89 can be a knob or lever that facilitates the translation of the dilator support arm 82 and hence the translation of the dilating member 84 along the needle's shaft 22. A surgeon can advance the dilating member 84 along the shaft 22 of the needle 20 and into the patient's tissue at a needle tip entry site. The release element 88 can release or detach the second positioning member 86 carried by the AECD 104 from the dilator's first positioning member 85, such that the needle 20 can be withdrawn from the patient's body and the dilating member 84.

In certain embodiments, one or more elements or devices that facilitate sensing operations can be carried or inserted within a patient's body. More particularly, a set of sensing elements or devices can be advanced into, carried by, or advanced through the shaft 22 of a needle or probe 20, such that particular types of signals and/or substances can be detected within the probe 20; at or proximate to the probe's tip 24; or at a location beyond the probe's tip within the patient's body. Sensing elements or devices suitable for internal bodily use can include one or more of optical fibers, optical detectors, ultrasonic transducers, ultrasound detectors, electrical leads, electrical sensors, pressure sensors, chemical sensors, and/or other devices. Portions of an AECD 100, 102, 104 can be configured to accommodate and/or interoperate with internal bodily sensing elements or devices, as further detailed hereafter.

Figure 4A:
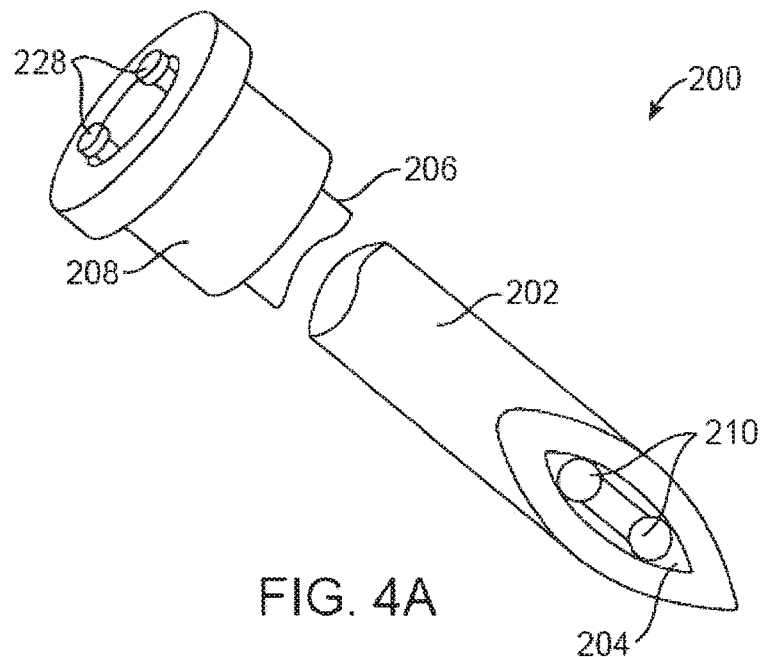
FIG. 4A is a perspective illustration of a probe carrying a set of sensing elements according to an embodiment of the disclosure.

FIG. 4A is a perspective illustration of a probe 200 carrying a set of sensing elements 210 according to an embodiment of the disclosure. The set of sensing elements 210 can include, for instance, one or more optical fibers, optical emission or detection devices, electrical leads, electrodes or electrical contacts, pressure sensors, ultrasonic transducers or ultrasound detectors, biological or chemical substance sensors, or other elements. In an embodiment, the probe 200 includes a shaft 202 having a distal segment or tip 204, and a proximal end 206 that is coupled to a probe sensing fitting 208. The probe sensing fitting 208 can include a Luer or other type of adapter, connector, sleeve, collar, or lock that carries, surrounds, or encapsulates a portion of the set of sensing elements. The probe sensing fitting 208 can include or correspond to, for instance, a female Luer lock fitting.

At least a portion of the set of sensing elements 210 is carried by the probe's shaft 202. The set of sensing elements 210 is coupled to the probe sensing fitting 208 in a manner that facilitates sensed signal communication with the AECD 100, 102, 104, as further detailed below with reference to FIG. 4B.

The set of sensing elements 210 can include a set of signal interface elements or structures 228 that are carried by the probe sensing fitting 208 to facilitate signal communication with the AECD 100, 102, 104. For instance, the set of signal interface elements 228 can include one or more of an optical fiber interfaces or lens, or an electrical contact or pin. Such signal interface elements 228 can reside at predetermined positions relative to the probe sensing fitting 208, and mate with a particular portion of the AECD 100, 102, 104 in a specified manner to facilitate reliable signal communication.

In an embodiment, the probe's shaft 24 can be substantially or completely obstructed to prevent fluid communication between the probe's tip 204 and proximal end 206. In another embodiment, the probe's shaft 202 can include a conduit therethrough to facilitate such fluid communication. In an embodiment in which the probe's shaft is substantially hollow or includes a conduit, a bodily fluid can flow or be drawn into the AECD 100, 102, 104 for sensing or analysis, and/or into a syringe 50 that is coupled to the AECD 100, 102, 104.

Figure 4B:
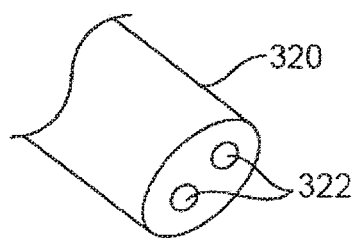
FIG. 4B is a perspective illustration of a device sensing fitting configured for signal communication with a probe sensing fitting according to an embodiment of the disclosure.

FIG. 4B is a perspective illustration of an AECD sensing fitting 320 configured for signal communication with a probe sensing fitting 208 according to an embodiment of the disclosure. In an embodiment, the AECD sensing fitting 320 includes one or more coupling, fitting, securing, retaining, or connecting structures that carry set of signal interface elements 322. Such coupling structures can include a Luer or other type of adapter, taper, collar, slip, connector, or lock structure. For instance, the AECD sensing fitting 320 can include or correspond to a male Luer lock structure.

The signal interface elements 322 carried by the AECD sensing fitting 320 are configured to structurally mate with and functionally correspond to the signal interface elements 228 carried by the probe sensing fitting 208. Thus, the signal interface elements 322 carried by the AECD sensing fitting 320 and the signal interface elements 228 carried by the probe sensing fitting 208 are structural and functional counterparts that facilitate consistently reliable error free signal transfer between the set of sensing elements 210 carried by the probe 200 and the AECD 100, 102, 104.

In addition to the foregoing, certain devices or elements that facilitate sensing operations and which are inserted into and carried within a patient's body can be coupled to a remote or external device 90, 92, such that they extend from a location within the patient's body into and through the AECD 100, 102, 104 to the remote or external device 90, 92, e.g., by way of the AECD's auxiliary access port 122. Such devices or elements can include, for instance, optical fibers, electrical leads, or guidewires that carry sensing elements, as further detailed below with reference to FIGS. 5A-5B.

Figure 5A:
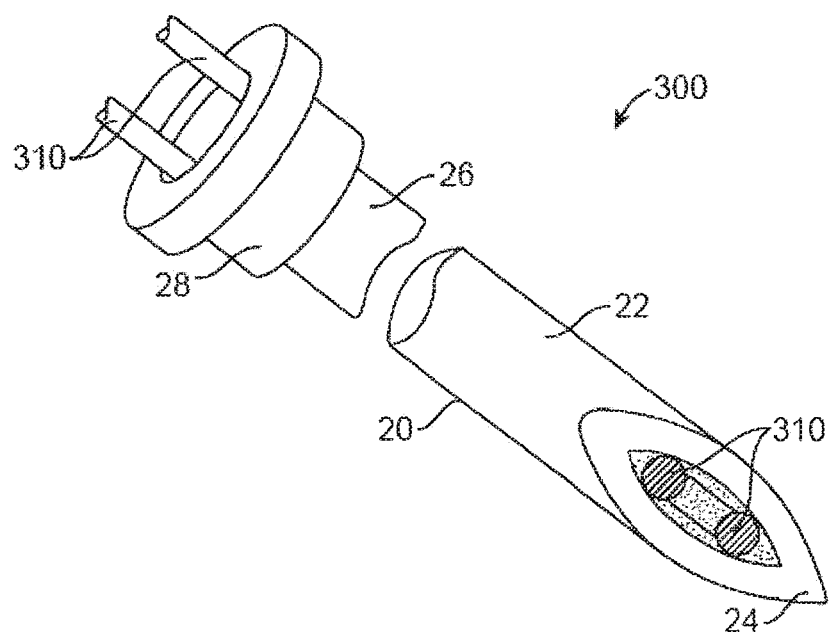
FIG. 5A is a perspective illustration of a probe or needle carrying a set of optical fibers and/or a set of electrical leads, respectively, according to an embodiment of the disclosure.

FIG. 5A is a perspective illustration of a probe or needle 20 carrying a set of sensing elements 300 according to an embodiment of the disclosure. Such sensing elements 300 can include, for instance, one or more optical fibers and/or electrical leads that extend through the probe or needle 20, depending upon embodiment details. Such sensing elements 300 can further include one or more distal signal transfer elements or devices 310. For instance, distal signal transfer devices 310 in an embodiment involving optical fibers can include one or more lenses, diffraction gratings, or other optical elements positioned at, proximate to, or beyond the tip 24 of the probe or needle 20. In an embodiment involving electrical leads, distal signal transfer devices 310 can include particular types of electrical, biological, or chemical sensing elements (e.g., an electrical sensor, a pressure transducer, or an ultrasonic transducer) carried at, proximate to, or beyond the probe's tip 24. A given optical fiber, optical element, electrical lead, and/or sensing element can be retained or secured at a predetermined position within the probe or needle 20 (e.g., proximate to the probe's tip 24 and/or proximate to the probe's coupling structure 28). In general, a group of optical fibers and/or electrical leads can be coupled or bundled to facilitate ease of insertion into an AECD's auxiliary access port 122, through the AECD 100, 102, 104, and into the probe or needle 20. A remote or external end of the set of optical fibers and/or electrical leads can be coupled to a remote or external computer system or medical device 90, 92.

Figure 5B:
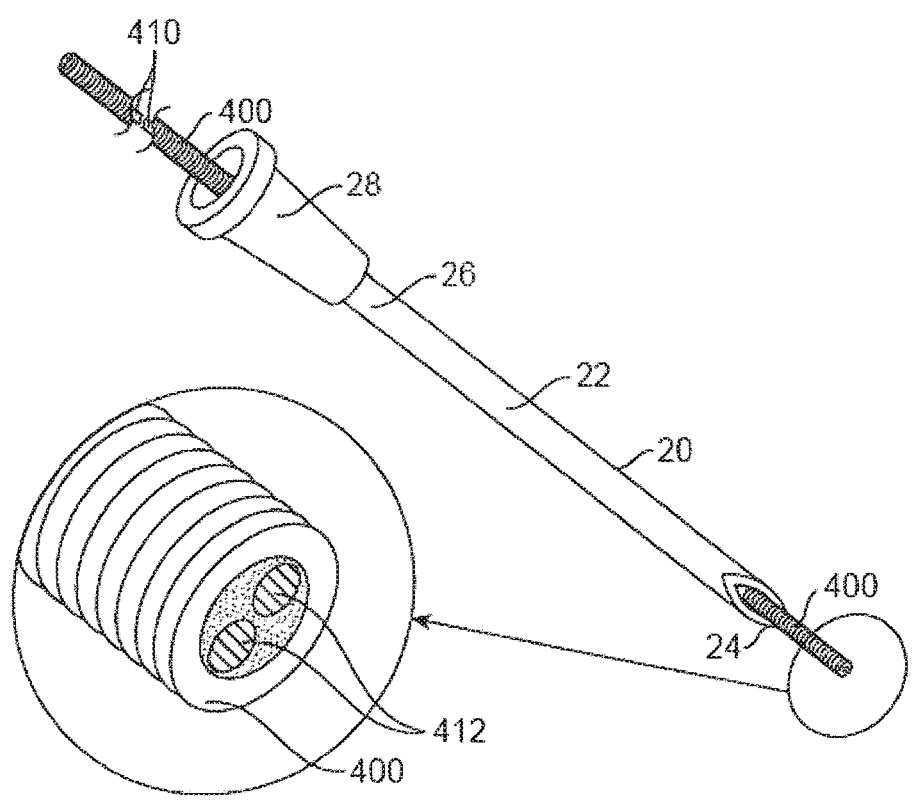
FIG. 5B is a perspective illustration of a needle carrying a sensing guidewire according to an embodiment of the disclosure.

FIG. 5B is a perspective illustration of a needle carrying a sensing guidewire 400 according to an embodiment of the disclosure. In an embodiment, the sensing guidewire 400 can carry, for instance, a set of optical fibers and/or electrical leads 410, as well as a corresponding set of optical elements and/or sensing devices 412 at a terminal or distal segment or end of the optical fibers or electrical leads, respectively. A sensing guidewire 400 can be inserted into and through an AECD 100, 102, 104 and into a probe or needle 20 in a manner previously described. A remote or external end of the sensing guidewire 400 can be coupled to a remote or external computer system or medical device 90, 92.

Aspects of Representative Integral Embodiments

In certain embodiments, one or more portions of an apparatus or device for indicating or verifying a probe tip location can be integrally carried by portions of a probe, a syringe, or another apparatus or device. In the description that follows, the recitation of a reference number that is identical or analogous to a reference number recited in relation to one or more of FIGS. 1A-5B indicates an element that is identical or analogous that previously described.

Figure 6A:
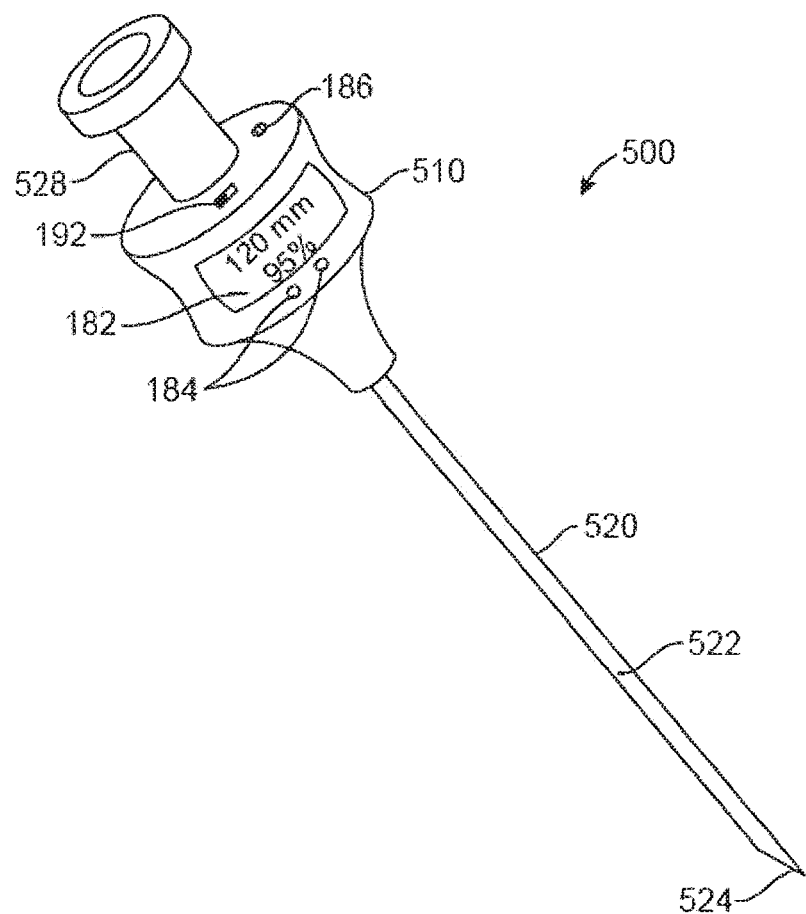
FIG. 6A is a perspective illustration of a needle device according to an embodiment of the disclosure.

FIG. 6A is a perspective illustration of a representative AECD needle assembly or needle AECD 500 according to an embodiment of the disclosure. In an embodiment, the needle AECD 500 includes a needle portion 520 that is integrally coupled to an AECD portion 510. The needle portion includes a shaft 522 and a distal end or tip 524. A coupling structure 528 such as a Luer type fitting, which can facilitate coupling to a syringe 50, can be carried by the AECD portion 510. The needle portion 520 includes a bore or conduit therethrough, which extends between the tip 524 and the coupling structure 528. In an embodiment, a section of the needle portion's bore forms a passage 532 within the AECD portion 510.

The AECD portion 510 internally carries a sensing unit 140, a processing unit 160, a memory 170, and a power source 190, in a manner analogous to that described above with reference to FIGS. 1B and 1C. One or more of the sensing unit 140, the processing unit 160, and the memory 170 can be coupled to an output unit 180 that includes a set of output devices or elements such as an LCD display 182, a set of LEDs 184, and/or an audio device 186. The LCD display 182 and the set of LEDs 184 can be carried in a manner that respectively facilitates the transmission or propagation of visual LCD and LED signals generated thereby external to the needle AECD 500. Similarly, the audio device 186 can be carried by the needle AECD 500 in a manner that facilitates the transmission or propagation of audio signals generated thereby external to the needle AECD 500. An activation switch 192 can selectively couple the sensing unit 140, the processing unit 160, the memory 170, and the output unit 180 to the power source 190.

Figure 6B:
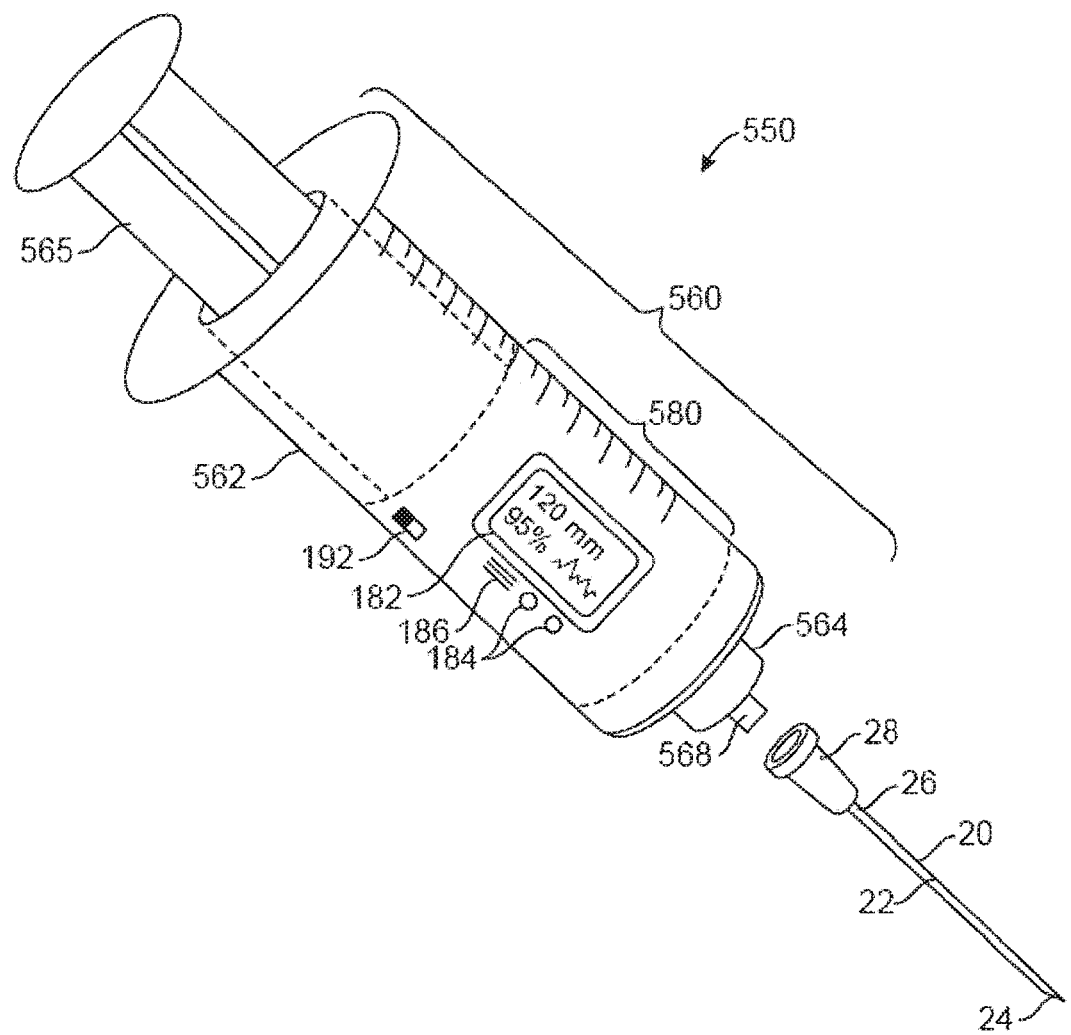
FIG. 6B is a perspective illustration of a syringe device according to an embodiment of the disclosure.

FIG. 6B is a perspective illustration of a representative AECD syringe assembly or syringe AECD 550 according to an embodiment of the disclosure. In an embodiment, the syringe AECD 550 includes a syringe portion 560 having a hollow or generally unobstructed shaft 562 in which a plunging element 565 can travel or reside. The shaft 562 includes a distal portion or end 564 that carries a coupling or fitting structure 568, such as a Luer type fitting, which can facilitate coupling to a needle 20. The shaft 562 of the syringe portion 560 integrally carries an AECD portion 580 that is configured in a manner that is identical or similar to that described above for the needle AECD 500.

Figure 6C:
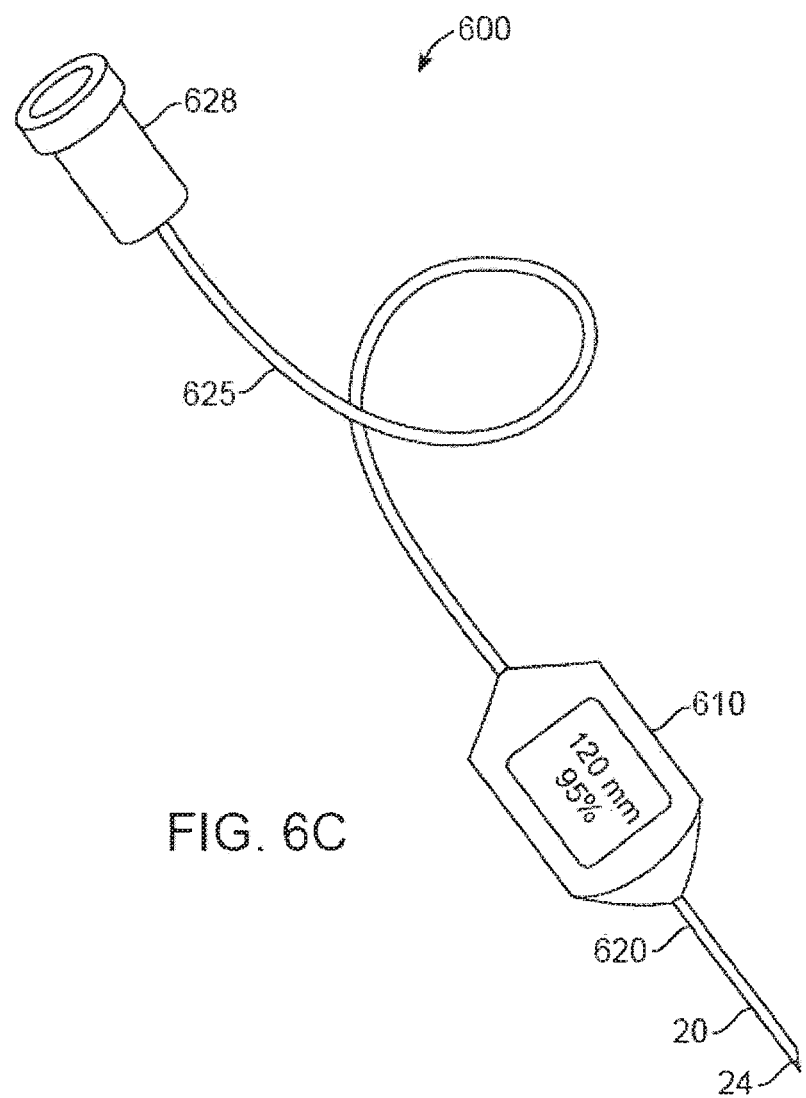
FIG. 6C is a perspective illustration of a device according to an embodiment of the disclosure.

FIG. 6C is a perspective illustration of a line-based AECD assembly or an in-line AECD 600 according to an embodiment of the disclosure. In an embodiment, the in-line AECD 600 includes an AECD portion 610 that is structurally and/or functionally analogous to one or more AECD embodiments 100, 102, 104, 500, 510 described above, but which is detachably or nondetachably coupled to a flexible or rigid first tube or line 620 and/or a second line 625. The first tube or line 620 can be coupled to a needle 20, and the second line 625 can be coupled to a line fitting or coupling (e.g., a Luer type fitting) 628. A bodily fluid can flow between the needle tip 24, the first tube or line 620, and the second line 625 by way of passing through the AECD portion 610. In an embodiment, the first tube or line 620 can be omitted, such that the AECD portion 610 is directly coupled to the needle 20.

Aspects of Representative Probe Location Indication Processes

Relative to a physiologic parameter of interest, a given patient population can exhibit a range of physiologic parameter values, particularly when different patient subpopulations are considered, such as typical, normal, or healthy patients as well as less typical, abnormal, or health-impaired patients. For instance, particular physiologic parameter value ranges that can be relevant to a vascular access procedure are shown below with reference to Tables 1-3; and certain physiologic parameter value ranges that can be relevant to a lumbar puncture procedure are shown below with reference to Table 4.

Table 1 illustrates representative venous and arterial blood pressure ranges associated with patient states corresponding to low blood pressure conditions, normal blood pressure conditions, and high blood pressure conditions.

TABLE 1

Expected Venous versus Arterial Pressure Conditions

| Vessel Type | Low Pressure | Normal Pressure | High Pressure |
|---|---|---|---|
| Vein | <5 mm Hg | 5-25 mmHg | 25-40 mmHg |
| Artery | 45-55 mm Hg | 55-160 mm Hg | 160-225 mm Hg |

Table 2 illustrates representative venous and arterial pulse pressure variations, that is, typical or expected peak-to-minimum pulse pressure differences corresponding to veins and arteries.

TABLE 2

Expected Venous versus Arterial Pulse Pressure Variation

| Vessel Type | Pulse Pressure Variation |
|---|---|
| Vein | 2-10 mm Hg |
| Artery | >20 mm Hg (30-70 mm Hg) |

Table 3 illustrates representative venous and arterial hemoglobin oxygen saturation value ranges corresponding to low, normal, and high patient hemoglobin oxygen saturation conditions.

TABLE 3

Expected Venous versus Arterial Hemoglobin Saturation Conditions

| Vessel Type | Low Hemoglobin Saturation | Normal Hb Saturation | High Hb Saturation |
|---|---|---|---|
| Vein | 10-40% | 40-60% | >60% |
| Artery | 85-92% | 92-100% | N/A |

Table 4 illustrates representative values or value ranges of cerebrospinal fluid parameters that can be relevant to a lumbar puncture procedure for particular patient populations, including low, normal, and high parameter values corresponding to penetration pressure, protein concentration, glucose concentration, red blood cell concentration, and white blood cell concentration.

TABLE 4

Particular Expected Low, Normal, and High Parameter Values Relevant to Lumbar Puncture Procedures

| Parameter | Low Value | Normal Value | High Value |
|---|---|---|---|
| Opening Pressure (child) | <10 mm H$_2$0 | 10-100 mm H$_2$0 | >100 mm H$_2$0 |
| Opening pressure (adult) | <60 mm H$_2$0 | 60-250 (obese) mm H$_2$0 | >250 mm H$_2$0 |
| Protein (newborn) | N/A | <1.5 g/L | >1.5 g/L |
| Protein (adult) | <0.18 g/L | 0.18-0.58 g/L | >0.6 g/L |
| Red Blood Cells | N/A | None | |
| Glucose | N/A | 2/3 serum glucose | >300 mg/dL |
| White Blood Cells | N/A | 5-20 cells/mm$^3$ | >100 cells/mm$^3$ |

As a result of physiologic parameter variations such as those indicated in Tables 1-3 or Table 4 above, one or more reference or threshold physiologic parameter values or value ranges corresponding to target anatomical structures or substances, non-target anatomical structures or substances, and/or patient state conditions or categorizations can be stored in a portion of the memory 170 (e.g., in a data structure such as a table) that a program instruction sequence can access. For instance, FIG. 7 is a block diagram of a representative data structure or table 700 that stores data or values corresponding to a venous blood pressure threshold, an arterial blood pressure threshold, a venous hemoglobin saturation threshold, and an arterial hemoglobin saturation threshold according to an embodiment of the disclosure. In an embodiment, the data structure or table 700 can additionally store a venous pulse pressure variation threshold and an arterial pulse pressure variation threshold. Particular data values within the data structure or table 700 can reside in the memory 170.

A given reference physiologic parameter value or value range can respectively represent a value transition level or value interval that facilitates a categorization or mapping of a non-reference physiologic parameter value in accordance with an anatomical environment, tissue, or substance type, where the non-reference physiologic parameter value was sensed, measured, calculated, or estimated using one or more sets of sensing signals generated by the sensing unit 140. In an embodiment, if a non-reference sensed physiologic parameter value is below an upper reference physiologic parameter limit, above a lower reference physiologic parameter limit, or within a reference physiologic parameter value range corresponding to or indicative of a given type of anatomical environment, the non-reference sensed physiologic parameter can be defined as corresponding to or indicative of the anatomical environment.

A program instruction sequence can evaluate or analyze a set of sensed parameter values at one or more times relative to at least a subset of reference physiologic parameter values or value ranges, after which an output unit 180 can present a number of notification and/or alert signals that indicate or convey a) a type of environment, tissue, or substance in which the needle tip 24 presently resides (e.g., a target anatomical environment, or a non-target anatomical environment); b) a likelihood of whether the needle tip 24 remains positioned at or within a target or a non-target environment, tissue, or substance during portions of a medical procedure; and/or b) patient state information. Representative processes for determining a probe tip position and/or patient state information and providing corresponding notification or alert signals are described in detail hereafter with reference to FIGS. 8-9.

Figure 8:
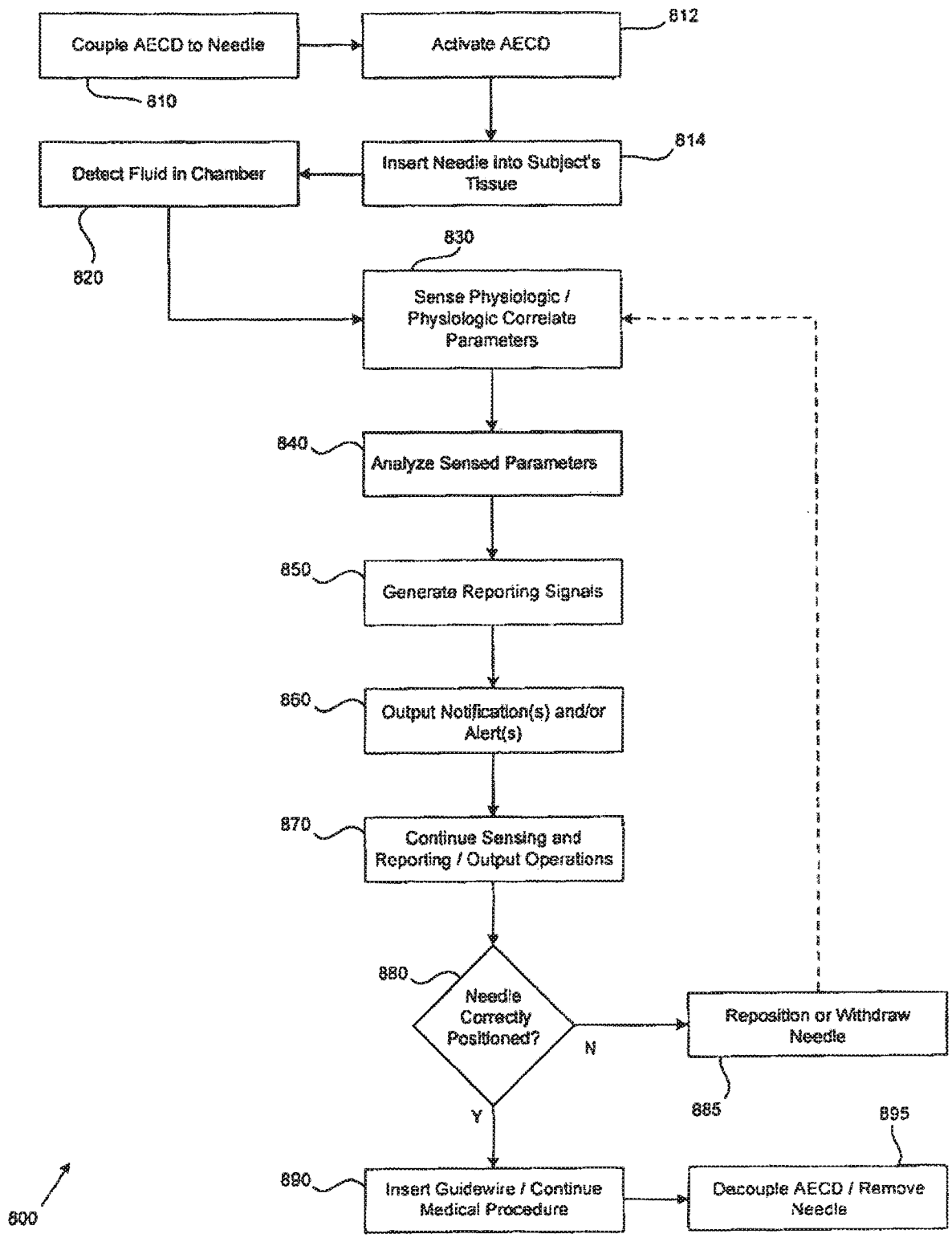
FIG. 8 is a flow diagram of a vascular target identification or verification process according to an embodiment of the disclosure.

FIG. 8 is a flow diagram of a process 800 for indicating probe or needle tip positioning relative to a target vascular structure or substance according to an embodiment of the disclosure. Particular portions of the process 800 can be performed, for instance, by way of a processing unit's execution of program instructions. In an embodiment, the process 800 includes a first process portion 810 that involves coupling an AECD 100, 102, 104 to a probe or needle 20, and possibly coupling the AECD 100, 102, 104 to a syringe 50. A second process portion 812 involves activating the AECD 100, 102, 104 (e.g., by way of the activation switch 192), and a third process portion 814 that involves inserting the probe or needle 20 into the patient's tissue.

The process 800 further includes a fourth process portion 820 that involves detecting the presence of a bodily substance or fluid within the AECD's chamber 130, for instance, by detecting a change in an optical signal and/or a chamber pressure transition (e.g., by way of a photodetector 152 and/or a piezoelectric transducer 144) that results from a bodily fluid flowing or being drawn from the probe or needle tip 24 through the bore of the probe or needle 20 and into the chamber 130. The process 800 also includes a fifth process portion 830 that involves sensing, detecting, measuring, determining, or estimating a set of physiologic or physiologic correlate parameters corresponding to the fluid in the chamber 130, for instance, one or more of an instantaneous or average fluid pressure, a maximum fluid pressure variation or range, and a set of optical parameters that are correlated with a hemoglobin oxygenation state.

A sixth process portion 840 involves characterizing, evaluating, or analyzing the set of sensed or measured physiologic parameter values corresponding to the fluid within the chamber 130. In an embodiment, the sixth process portion 840 can involve a transformation or conversion of particular sensed physiologic parameter correlate values to a measure or estimate of a value for a physiologic parameter. For instance, the sixth process portion 840 can involve a determination or estimation of an oxygenation, deoxygenation, or other gas saturation state based upon sensed or measured optical signals in view of reference optical absorbance spectra data. In an embodiment, the sixth process portion 840 further involves a comparison of sensed or measured parameter values relative to one or more reference or threshold physiologic parameter values stored in a memory 170 (e.g., within a data structure 700) to facilitate discrimination between venous and arterial blood, and hence discrimination between a probe or needle tip positioning within a vein or an artery. For instance, if the sensed or measured parameter values indicate an average pressure of less than approximately 40 mmHg, a pressure variation of less than approximately 15 mmHg, and a hemoglobin oxygen saturation of less than approximately 60%, the sixth process portion 840 can determine that the probe or needle tip 24 resides in a vein. If the sensed or measured parameter values indicate an average pressure of greater than approximately 45 mmHg, a pressure variation of greater than approximately 20 mmHg, and a hemoglobin oxygen saturation of greater than approximately 80%, the sixth process portion 840 can determine that the probe or needle tip 24 resides in an artery.

In an embodiment, if a comparison, evaluation, or analysis of one or more Sensed or measured parameters relative to a set of reference parameter values gives rise to uncertainty in a tissue or fluid type determination, the sixth process portion 840 can generate a likelihood or confidence value corresponding to the tissue or fluid type determination. Such a likelihood or confidence value can be included in a set of reporting signals for subsequent presentation or display (e.g., as a notification signal) to a surgeon or other medical professional.

A seventh process portion 850 involves generating and transferring or issuing reporting signals to an output unit 180, where the reporting signals can correspond to or include notification and/or alert signals. An eighth process portion 860 involves the presentation of notification and/or alert signals using one or more output devices, for instance, in one or more manners previously described. By way of the eighth process portion 860, a) an LCD 182 or other display device can present or output sensed, measured, or estimated physiologic parameter values; and/or b) a set of LEDs 184 or an audio device 186 can be activated to indicate that the tip 24 of the probe or needle 20 resides in a target or non-target type of bodily tissue or fluid. In an embodiment, a confidence value can be indicated by the LCD 182 or the set of LEDs 184.

A ninth process portion 870 involves repeating the fifth through eighth process portions 830-860 such that updated notification and/or alert signals can be presented on a continuous or periodic basis. The ninth process portion 870 can facilitate a determination of whether the probe or needle tip 24 remains in a target or intended type of bodily tissue or fluid, or has moved into a non-target or unintended type of bodily tissue or fluid.

A tenth process portion 880 involves determining whether the needle 20 is correctly positioned or located in a target or intended bodily tissue or substance. If not, an eleventh process portion 885 can involve repositioning or withdrawing the needle 20. Depending upon embodiment details or the nature of a medical procedure under consideration, the process 800 can return to the fifth process portion 830 in association with a needle repositioning or withdrawal.

Upon indication or confirmation of a target, intended, or desirable probe or needle tip positioning (e.g., based upon notification and/or alert signals), a twelfth process portion 890 can involve the insertion of a guidewire or a set of optical fibers into the AECD's auxiliary access port 122, through the AECD 100,102,104, and into or through the bore of the probe or needle 20. In an embodiment, a thirteenth process portion 895 involves removal of the AECD 100, 102, 104 and/or the probe or needle 20, and continuation of a medical procedure under consideration.

Figure 9:
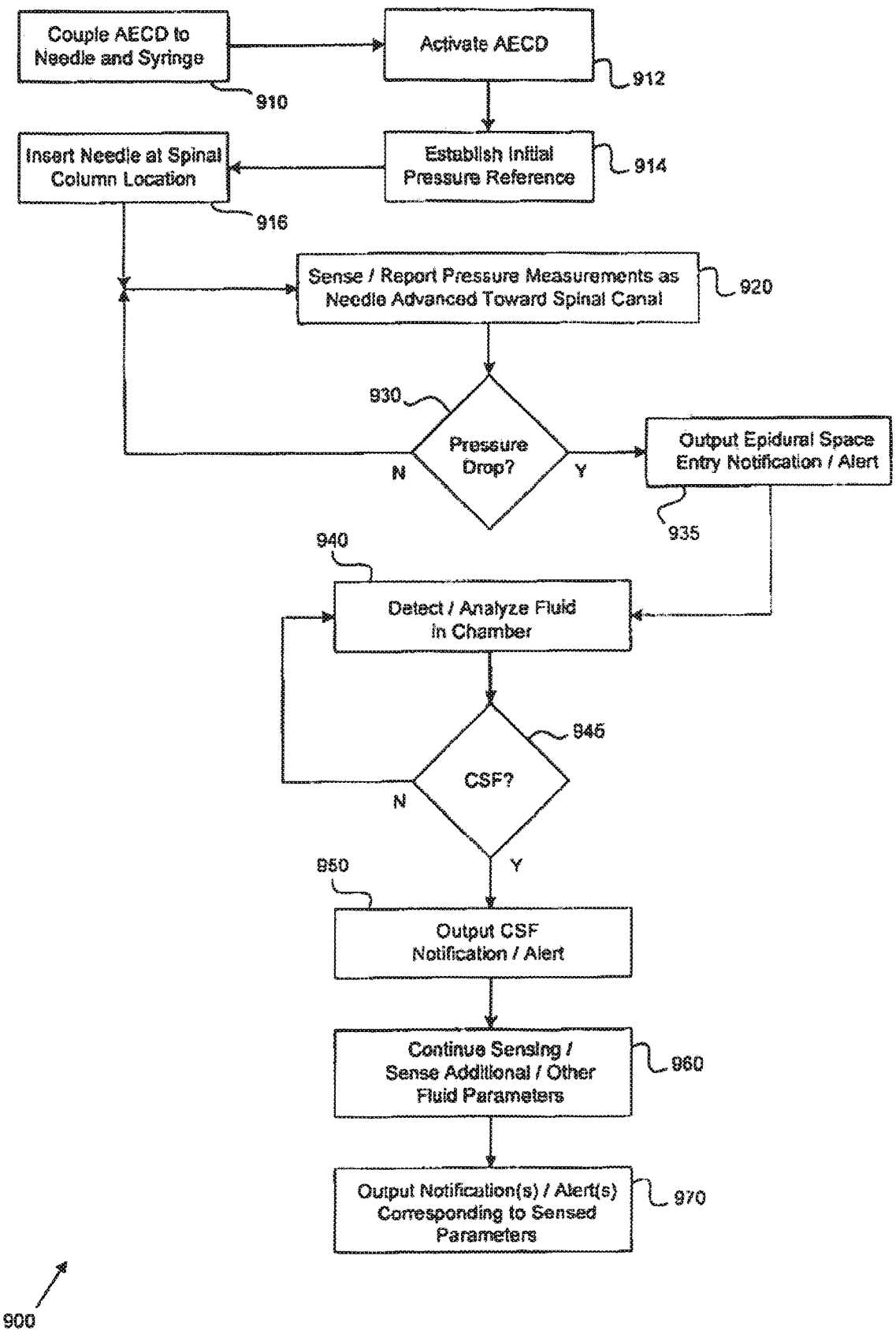
FIG. 9 is a flow diagram of a lumbar puncture target identification and/or lumbar puncture parameter reporting process according to an embodiment of the disclosure.

FIG. 9 is a flow diagram of a spinal or lumbar puncture target identification and/or spinal or lumbar puncture parameter reporting process 900 according to an embodiment of the disclosure. In an embodiment, the process 900 includes a first process portion 910 that involves coupling an AECD 100, 102, 104 to a needle 20 and further coupling the AECD 100, 102, 104 to a syringe 50. A second process portion 912 involves activating the AECD 100, 102, 104. A third process portion 914 involves establishing an initial pressure reference value by measuring a pressure in the AECD's chamber 130. Depending upon embodiment details, the third process portion 914 can involve drawing air through the bore of the needle 20, into and through the AECD 100, 102, 104, and into the syringe 50, thereby correspondingly establishing an air column between the tip 24 of the needle 20 and the AECD's chamber 130. Alternatively, the third process portion 914 can involve establishing a fluid column between the needle's tip 24 and the chamber 130, for instance, by drawing a saline solution into the AECD 100, 102, 104. A fourth process portion 916 involves inserting the probe or needle 20 into the patient's tissue at a lumbar or other spinal column location.

A fifth process portion 920 involves continuously or periodically sensing pressure values and issuing reporting signals to the output unit 180, where such reporting signals include or correspond to sensed or measured pressure values, such that a surgeon or medical professional can control or maintain a known or approximately constant needle insertion pressure while the needle 20 advances through non-target tissue such as a ligament (e.g., the Ligamentum flavum) toward the spinal canal. In an embodiment, a sixth process portion 930 involves determining whether a pressure drop (e.g., approximately a 5-15 mmHG pressure change) expected to correspond to needle tip entry into the epidural or extradural space has occurred, for instance, by analyzing a set of prior sensed pressure values relative to a set of most recent sensed pressure values or a current sensed pressure value. If such a pressure change has occurred, a seventh process portion 935 involves outputting notification and/or alert signals to indicate that epidural space entry has occurred. Such notification or alert signals can be provided by way of an LCD 152, a set of LEDs 154, and/or an audio device 156.

An eighth process portion 940 involves detecting the presence of a fluid in the chamber 130 following an indication that the needle tip 24 has entered the epidural space (e.g., after the aforementioned pressure drop, where the presence of a fluid in the chamber 130 can arise from further penetration of the needle tip 24 into the subdural or subarachnoid space), and a ninth process portion 945 involves determining whether the fluid present in the chamber 130 is cerebrospinal fluid. In an embodiment, the eighth and ninth process portions 940, 945 can include sensing or detecting one or more physiologic characteristics, properties, or parameter values corresponding to the fluid in the chamber, such as a pressure value, a protein concentration value, and a glucose value, and evaluating or analyzing such sensed physiologic parameter values relative to corresponding reference values for cerebrospinal fluid, where such reference values can be stored in the memory 170.

If the sensed physiologic values indicate that the fluid in the chamber 130 is cerebrospinal fluid, a tenth process portion 950 involves outputting notification and/or alert signals (e.g., by way of an LCD 152, a set of LEDs 154, and/or an audio device 156) to indicate that cerebrospinal fluid has been detected. The tenth process portion 950 can include displaying a CSF pressure value or an opening pressure value.

In an embodiment, an eleventh process portion 960 can involve sensing, detecting, measuring, or estimating a number of cerebrospinal fluid physiologic parameter values, such as one or more of a presence or concentration of red blood cells, a presence or concentration of white blood cells, and a set of optical absorbance values that can correspond to fluid color or clarity. Finally, a twelfth process portion 970 can involve outputting notification and/or alert signals corresponding to such physiologic parameter values.

In one embodiment, a device can include a sterile, disposable, lightweight, inexpensive, compact, self-contained pressure sensor with integrated display that can connect to a standard needle or catheter on one end (e.g., distal portion) and to a syringe on the opposite end (e.g., proximal portion). The term "syringe", as used herein, can include a standard syringe including a plunger fitting in a tube so as to provide a simple piston-pump, or more generally may refer to any pumping means couplable to the device and operable to elicit movement of a fluid through a coupled probe, such as drawing fluid proximally through the probe. The device can be used to identify probe location and/or tissue type based on parameters such as pressure properties, or to output/report pressure values to the user when attached to a catheter or needle placed in a pressurized area in the body (e.g. blood pressure, CSF pressure, pleural fluid pressure, compartment pressure).

Devices of the present invention will typically include a display for outputting/reporting via visual display of detected biological parameters, such as pressure and/or changes thereof indicative of probe location. The display may be carried by the housing of a device such that the detected biological parameters are easily or conveniently viewed by a user during operation of the device. In one embodiment, the display is angled proximately or oriented at an angle to the plane of the device/needle so that the display can be easily read during a procedure, e.g. providing an advantage during certain procedures where a flat display might be difficult to visualize (e.g., during internal jugular cannulation). Further, devices typically include a configuration that, when in assembly with a probe and/or syringe, is axially aligned or substantially "in-line" with the needle and syringe. Such a configuration in many cases demonstrates to be more ergonomic, and can advantageously offer improved functionality, for example, by permitting the user to actively view both the display and target area during use, thereby reducing user movement associated with viewing of a remote display, and limiting unwanted probe movement or resulting injury to the patient due to inadvertent probe positioning or misplacement. Additionally, the axially aligned configuration can, in certain instances, increase device functionality and utility by allowing the user to more easily perform a procedure with one hand while reading the display.

Embodiments of the device can optionally include an integrated port for introducing a guidewire, e.g., as further described below. In such an embodiment, the port can include a seal that allows pressure transduction with or without a guidewire in the port, e.g., so as to provide a self-sealing port. Such an integrated guidewire port design can advantageously permit a user to introduce a guidewire into a target location or lumen while minimizing or eliminating exchanging of components and/or undesired probe movement, thereby further minimizing occurrence of error or patient injury due to probe misplacement.

Devices can include a channel (e.g., body fluid or blood channel) fluidly coupling a syringe port to a probe port. In an integrated guidewire port embodiment, the guidewire port can be fluidly coupled to the blood channel. The housing, or portion thereof, and blood channel may optionally include a translucent material design so that a body fluid can be visualized as it is drawn into the device housing. In certain indications, it may be desirable for the user to see a flash of bodily fluid (e.g., blood or CSF during vascular access and lumbar puncture procedures) during operation.

Figure 10A:
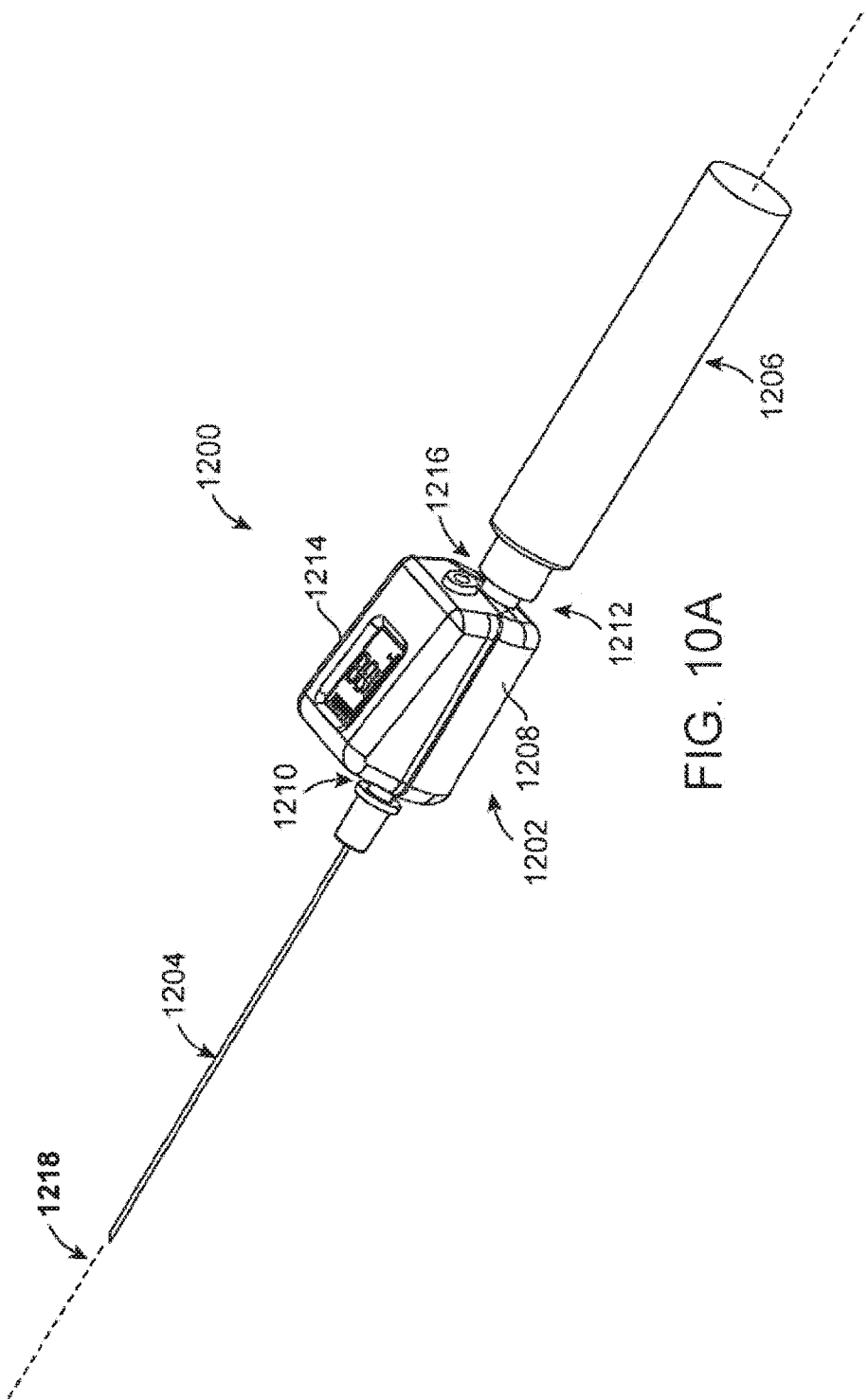
FIGS. 10A and 10B illustrates an assembly including a detection device coupled to a probe and a syringe, according to another embodiment of the present invention.
Figure 10B:
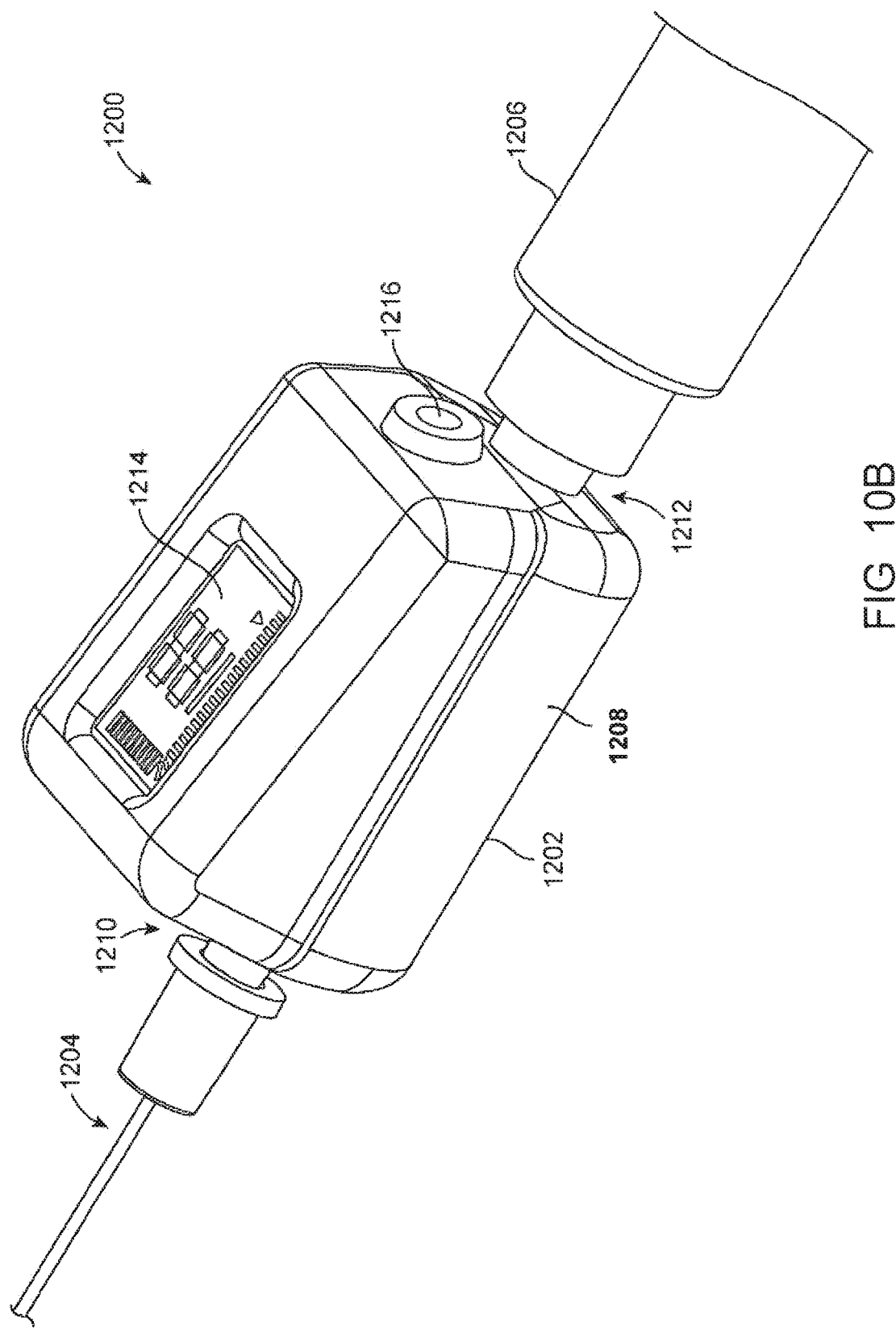

FIGS. 10A and 10B illustrate a detection device assembly, according to an embodiment of the present invention. The assembly 1200 includes a detection device 1202 coupled distally to a probe 1204 and proximally to a syringe 1206. The device 1202 includes a housing 1208 having a distal portion with a port 1210 that is detachably coupled to a probe 1204, and a proximal portion with port 1212 that is detachably coupled to a syringe 1206. Additional components, including those described above such as a sensing unit, processing unit, output unit, etc. (not shown), can be further carried by the housing 1208. A housing of a device can include a single piece or multipiece assembly. The device 1202 additionally includes a display 1214 for reporting or visually displaying a determined biological parameter, such as a pressure value. The device 1202 further includes a guidewire port 1216 integrated with or carried by the housing 1208.

A long axis 1218 of the assembly is shown to illustrate an axial alignment or in-line assembly of components, including the probe 1204 and syringe 1206 coupled with the device 1208. Components need not be limited to any particular positioning with respect to the long axis. But axial alignment or in-line assembly will generally refer to an ordered arrangement of certain components with respect to a long axis reference. In the embodiment illustrated in FIG. 10B (and additionally in certain embodiments described further herein), the assembly includes an in-line arrangement with the device 1208 disposed substantially between the coupled probe 1204 and the syringe 1206. Referring to the device 1202, certain components (e.g., sensing unit, processing unit, output unit, display, etc.) can be carried by the housing 1208 so as to be disposed substantially between port 1210 and port 1212. The display 1214 can be carried by the housing 1208 such that the display 1214 or surface thereof (e.g., outer surface) is at an angle with respect to the long axis 1218 of the assembly 1200. For example, the display can be angled proximately as illustrated in FIGS. 10A and 10B. Such a configuration of the display may be selected so as to allow a user, viewing the display from a location generally proximal to the device, to more easily view the display during operation.

In use, a user can manipulate or control positioning of the assembly while grasping or holding the assembly about the device 1202 and/or syringe 1206. The distal portion of the probe 1204 can be inserted into a tissue or body of a patient. With positioning, a biological parameter (e.g., pressure) of the environment in which the probe 1204 is positioned is detected or determined, and the parameter value or information output for visualization on display 1214. Device and assembly operation is further described elsewhere herein.

Figure 11:
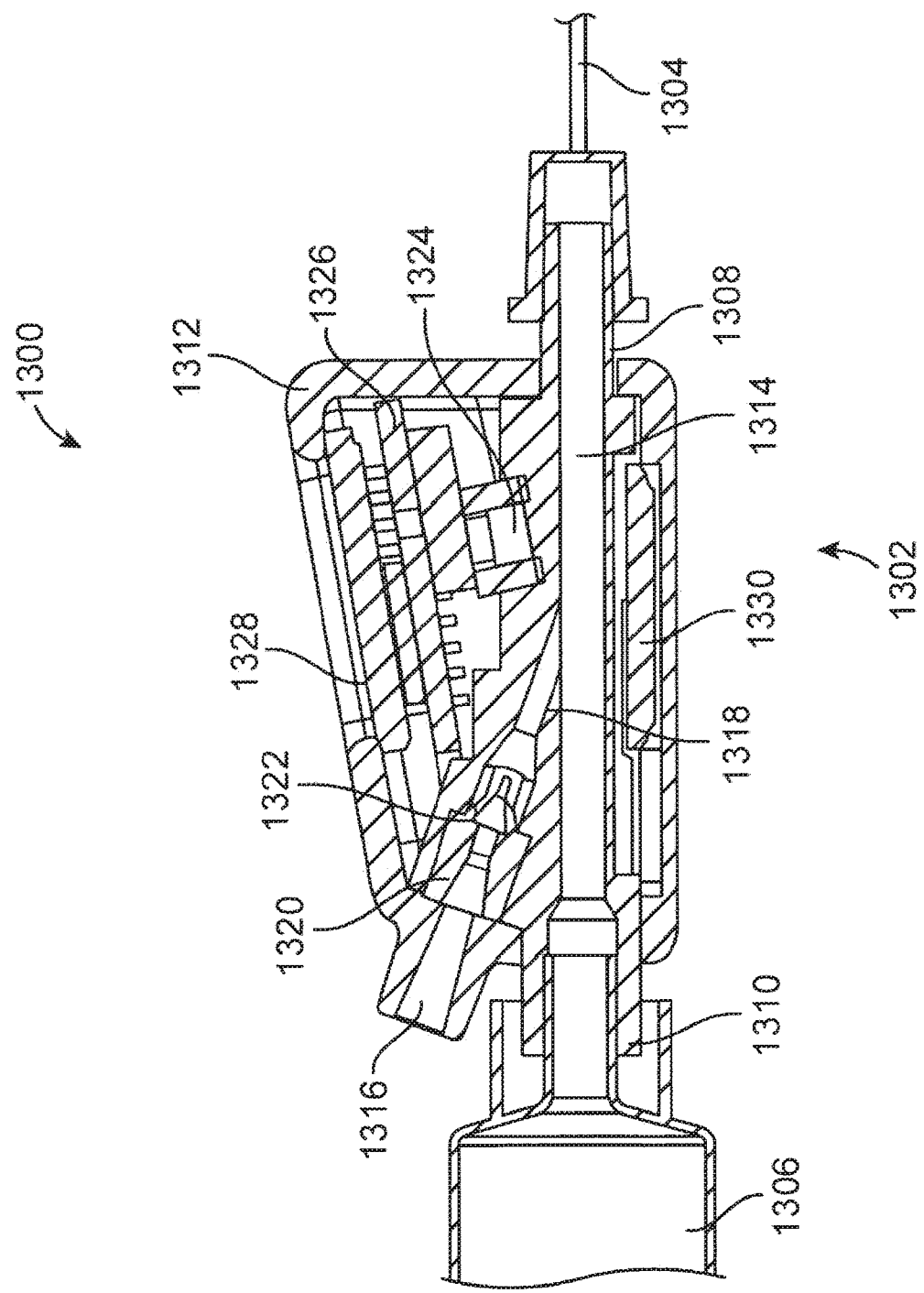
FIG. 11 is a diagram of an apparatus for indicating a probe segment or tip location, according to another embodiment of the present invention.

FIG. 11 shows a diagram of an apparatus (e.g., as in FIGS. 10A and 10B) for indicating a probe segment or tip location, according to another embodiment of the present invention. The assembly 1300 includes a device 1302 with a probe 1304 removably coupled to a distal portion of the device and a syringe 1306 removably coupled to a proximal portion of the device. The probe 1304 is coupled to the device about a port 1308 carried by housing 1312 including a distal male Luer fitting, and the syringe 1306 is coupled to the device about a port 1310 including a proximal female Luer fitting. Port 1310 and port 1308 are fluidly coupled about channel 1314. Channel 1314 and/or housing 1312 may be at least partially transparent or translucent exteriorly to the device so as to allow visualization of a fluid within channel 1314. The device 1302 further includes guidewire port 1316 fluidly connected to channel 1314 about guidewire port channel 1318. The guidewire port 1316 is in assembly with seal cup 1320 and seal 1322 so as to provide a self-sealing assembly. The device further includes sensor 1324 (e.g., pressure sensor) in operable communication with channel 1314 so as to enable detection of a parameter (e.g., pressure) of an environment in which probe 1304 is positioned. The device 1302 further includes electronics and signal processing components 1326 (e.g., similar to as described above), including a printed circuit board, processor, and the like, as well as power source 1330. Display 1328 is carried by the housing 1312 and angled proximally with respect to a long axis of the assembly.

As described above, a device of the present invention can optionally include an integrated port for introducing a guidewire, which may advantageously permit a user to introduce a guidewire into a target location or lumen while limiting additional component exchanging steps and/or undesired probe movement. Such simplification of the guidewire placement procedure can help minimize occurrence of error or patient injury due to probe misplacement, as illustrated with reference to FIGS. 12 through 14. FIGS. 12A through 12D illustrate probe tip location detection under ultrasound guidance, with FIGS. 12C and 12D illustrating component exchange steps that may elicit undesired movement of the probe positioned in the tissue and potential injury to the patient. FIGS. 13A through 13F illustrate probe tip location indication under pressure transduction (e.g. column manometry) guidance. Similar to ultrasound guidance techniques, pressure transduction guidance includes component exchanging (FIGS. 13E and 13F) that can cause undesired movement of the probe and potential patient injury.

Guidewire placement according to a method of the present invention using a device with an integrated guidewire apparatus is illustrated with reference to FIGS. 14A through 14C. As shown, such a method can include inserting the probe (e.g., a needle) into the tissue (FIG. 14A) and obtaining a measurement of the parameter(s) of interest (FIG. 14B). Following measurement, the guidewire placement can be accomplished by inserting the guidewire through the port and probe of the device and into the target body lumen of the patient (FIG. 14C). Guidewire placement can be accomplished while limiting or eliminating removal and/or exchanging of assembly components.

Figure 15:
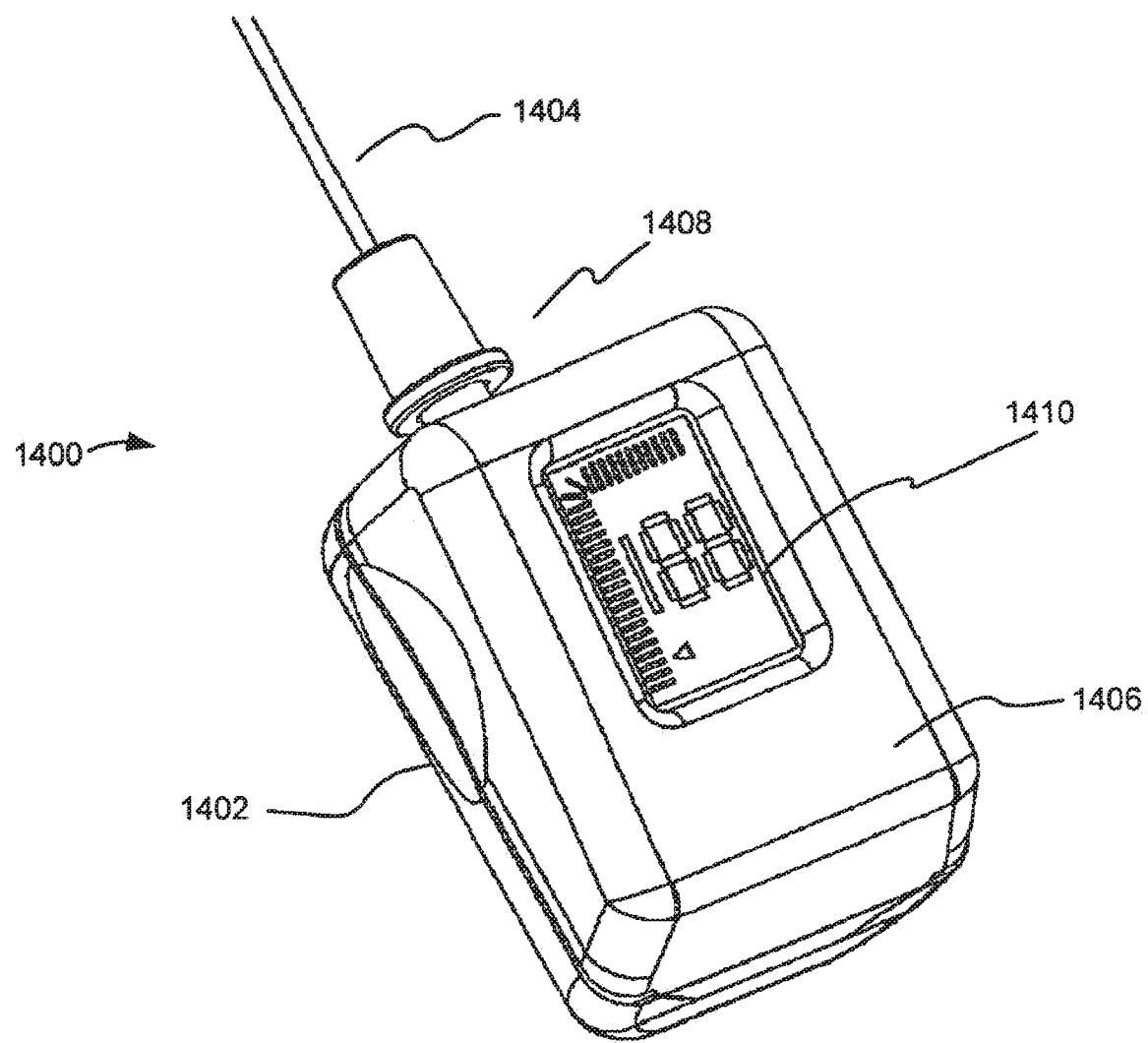
FIG. 15 illustrates an assembly including a detection device with a closed proximal portion and a distal portion coupled to a probe, according to an embodiment of the present invention.

In yet another embodiment, a device of the present invention can include a "closed" portion, such as a closed proximal portion lacking a port. FIG. 15 illustrates an assembly 1400 including a detection device 1402 coupled with a probe 1404. The device 1402 includes a housing 1406 including a distal portion and a proximal portion. The distal portion of the housing includes a port 1408 couplable to the probe 1404. The proximal portion of the device 1402 is closed in the sense that it lacks a port or opening. Additional components, including those described above such as a sensing unit, processing unit, output unit, etc. (not shown), can be further carried by the housing, with the housing of a device including a single piece or multipiece assembly. The assembly 1400 includes an "in-line" configuration with respect to the coupled probe 1404 and device 1402, similar to as described above. The device 1402 further includes a display 1410 carried by the housing 1406. The display 1410 may be disposed on the housing 1406 and angled proximally so as to allow more optimal viewing by a user during manipulation of the assembly 1400, such as positioning a distal portion of the probe 1404 in a tissue of a patient.

Devices of the present invention can be configured for operation in one or more of various different operational modes. In one embodiment, a device is operable in a tissue transition detection mode ("transition detection mode"). For example, the device can be configured to detect probe (e.g. a needle) distal tip location during blind needle insertion. In such operation, the pressure changes rapidly when the needle transitions from one site to another, provided the two sites have different pressures (e.g. from soft tissue to a vessel, from a vein to an artery, from a ligament to the epidural space, from a ligament to the CSF space). It has been observed that the pressure change at the tip of the needle is transduced through the air (or vacuum) already present in the device housing, and therefore an absolute pressure reading is available before the arrival of the body fluid into the device housing. The device display can be used to indicate tissue transitions, with the device configured such that the display updates at an appropriate rate. If the display updates at a constant rate (e.g. at 4 Hz), or if the display is displaying average pressure, rapid pressure changes may not be easily discerned by the user in some indications. Rather, a variable display rate makes pressure changes more apparent by introducing sudden, non-cyclical display changes that "stand-out" visually. For instance, if the probe is in soft tissue (e.g., pressure ~0 mm Hg), the display can update at 1 Hz. A near instantaneous (e.g. within 5 ms) change in the display reading upon entry into a vessel (e.g. from 0 mm Hg to 25 mmHg) can provide a visual cue to the user that a tissue boundary has been crossed. The device makes use of algorithms developed to determine when to update the display given a temporal set of pressure readings. In general, when the needle tip is in a static environment (e.g. in an artery), the display provides a mean pressure, using a moving average of the pressure readings over a given time period. However, if the needle is removed from a vessel, the display immediately reverts to an instant reading.

In another embodiment, a device can further include a stylet, e.g., for use in a lumbar puncture procedure. A stylet includes a solid metal core inserted into the needle to prevent entry of tissue into the needle bore during insertion or removal of the needle that may be used during lumbar puncture and epidural needle insertion. A device of the present invention may come with a custom stylet that inserts through the proximal end of the device housing, through the blood channel, and then through the needle so that it performs the same functions as existing stylets.

In another embodiment, a device can be configured for continuous monitoring at fixed location ("continuous monitoring" or "fixed location" mode). During continuous monitoring, different values of pressure are useful to the user, especially the mean pressure over a period of time, or the maximum and minimum values over a given period of time (i.e. systolic and diastolic pressure). Further embodiments may include a combination of different operation modes. For example, in some indications (e.g., vessel access, lumbar puncture, epidural catheter insertion), it may be desirable to switch (e.g., programmed or automatic switching) between these two modes-blind needle insertion and continuous monitoring.

Structures of the present invention can be configured for use for or in conjunction with various different methods or indications. Exemplary indication for which a device of the present invention can be configured to include or be used in conjunction, without limitation, with the following indications/procedures: blood vessel or body lumen access; catheter placement (e.g., central venous catheter insertion); oxygen saturation/blood pressure (BP) monitoring; lumbar puncture; epidural space detection and/or needle/catheter placement; thoracentesis (pressure monitoring); peripheral nerve block procedures; evaluation of vascular properties related to disease (e.g. ankle brachial pressure index and measurement of blood pressure in or around stenotic lesions); wireless pressure monitor; and compartment pressure detection/monitoring. Some exemplary indications and corresponding embodiment are described further below.

Blood Vessel Access: In this embodiment, the device functions to identify when and what type of vessel has been entered by the needle, and report pressure parameters for the vessel once the needle has entered it (e.g. mean pressure, magnitude of the pulse pressure). During needle insertion, the display and associated components (e.g., processing unit, instructions, algorithm) are optimized for making changes in tissue boundary (e.g., see transition detection mode above) readily identifiable to the user by varying the display update rate and the type of measurement displayed (e.g. mean pressure vs. instant pressure). A device can be programmed or configured such that once in a vessel, the display changes to a slower update rate, and displays the mean pressure (see, e.g., continuous/fixed location mode above). However, pressure is monitored and can be rapidly (e.g., 200 Hz) detected reported via output, e.g., with the display instantly changing if the needle is dislodged from the vessel or relocated. In the device embodiment including an integrated guidewire port, the port allows a guidewire to be inserted into the blood vessel while continuously monitoring pressure (the port has a low friction seal to keep guidewire tactile feel, but the port seals around the guidewire to allow accurate pressure monitoring).

Oxygen Saturation/EEG/EKG/BP Monitoring: The device can be used in patients with indwelling arterial catheters or with direct needle puncture of an artery. In one embodiment, the distal port of the device connects to the catheter or needle. The proximal end is sealed (e.g., does not include an additional port such as a syringe or guidewire port). The device optionally contains an electrical connector that attaches to standard pulse oximetry probes (e.g. a finger tip probe that contains one or more LED's for determining oxygen saturation). The device provides power to the oximetry probe, and also receives the (electrical) signal from the LED's and uses processing instructions or an algorithm to determine the oxygen saturation of the blood. Optionally, the device contains an electrical connector that attaches to standard EEG and/or EKG leads. The device receives and interprets the electrical signals from the EEG and/or EKG leads. The device can receive or monitor a single parameter or a plurality of different parameters. For example, the blood oxygen saturation, EEG, EKG, and/or various blood pressure/pulse measurements (e.g. mean pressure, pulse rate, systolic pressure, and/or diastolic pressure) are displayed on the integrated display. The device can transmit the signal to a remote device or monitoring display.

Lumbar Puncture (Access and CSF Reading): The present invention further includes methods and structures for performing lumbar puncture procedures. Currently, physicians use a glass or plastic column manometer to measure pressure during lumbar puncture. The technique is awkward, risks dislodging the needle, and is time-consuming and consequently many physicians do not measure the pressure during a lumbar puncture. A device according to an embodiment of the present invention can be configured to serve two functions in this application: identifying entry into the CSF space, and providing a continuous pressure measurement once inside the CSF. The processing instructions and/or algorithm for the lumbar puncture application can be similar to the vessel access application in that during the early part of the procedure, the display is in transition detection mode described above, that is, the display is optimized for detecting transition of the needle tip from the ligament into the CSF space. If no pressure is applied, the pressure will transition from a low (0 mm Hg) pressure reading to a positive pressure reading (e.g. 10 mm Hg) when the needle transitions from the ligament into the CSF space. If positive pressure is applied when the needle is in the ligament (the fluid and/or air are prevented from leaving the needle tip when it is in the ligament) the pressure will go from a high (e.g. 50 mm Hg) value to a lower positive value (e.g. 10 mm Hg) upon entry in the CSF space. Once the needle has entered the CSF space, the display will provide a mean CSF pressure (the "opening pressure") and a "closing pressure" after CSF samples are removed. The graphical part of the display will demonstrate the pulsations of the CSF. The device will monitor the instant pressure, and will alert the user to needle dislodgment. During procedures where CSF is removed to decrease the intracranial pressure, the device provides the ability to monitor the CSF in real time (currently, the user needs to use a tube glass manometer, which is time consuming). See also, commonly owned U.S. application Ser. No. 12/806,747, now U.S. Pat. No. 8,814,807, filed Aug. 19, 2010, which is incorporated herein by reference.

A device may be further optimized for pediatric lumbar puncture. In such an embodiment, the device is modified (e.g., reduced) in size and weight (e.g. by using flexible circuits and display, etc.) so that it does not dislodge the spinal needle if it is not supported by the user.

Epidural Space Detection: The present invention further provides structures and related methods for detection of an epidural space, e.g., during epidural access procedures such as catheter placement and drug deliver. In one embodiment, the device can be used to better prevent two common mistakes—entry of the needle into the CSF, which causes severe headaches, and mistaking the muscle or other soft tissue for the epidural space, which results in failed anesthesia (the epidural catheter is mistakenly inserted into the muscle instead of the epidural space). During an epidural procedure, the needle passes through the skin and fat, ligament, and finally enters the epidural space. The needle can enter muscle if it is not inserted in the midline or the needle can enter the CSF space if it is inserted too far. Currently, a "loss-of resistance" is used to identify entry into the epidural space and prevent the needle from continuing into the CSF space. Instead, pressure can be used to identify the epidural space (either a loss of pressure if a pressurized fluid is used, or a change from zero pressure to positive pressure if the needle is advanced without a pressurized fluid or air column). Muscle can be differentiated from the epidural space by the absence or presence of a positive pressure epidural waveform.

Thoracentesis (Pressure Monitoring): Thoracentesis is a procedure where a large needle is inserted into the pleural space outside the lung to drain accumulated fluid. Physicians face a dilemma when performing the procedure: too little fluid removal will not relieve symptoms whereas too much fluid removal can result in a deadly condition known as re-expansion pulmonary edema. Because of the risk of developing pulmonary edema, most physicians remove no more than 1-1.5 Liter of fluid during a given procedure. However, this practice often leads to poor symptom relief, and many patients require multiple procedures to feel better.

In another embodiment of the present invention, a device can be configured and utilized to monitor the procedure including measuring the pressure rather than the amount of fluid removed. Using a target pressure (e.g., selected from those reported in the literature) to determine when to stop the procedure (−20 cm H20), the optimal amount of fluid is removed while preventing the complications related to either too much or too little fluid withdrawal. Despite solid clinical evidence collected over the past two decades that support measuring pressure, adoption has been limited because the correct tools simply don't exist. The current device will allow physicians to precisely and continuously monitor fluid pressure during thoracentesis. The device can optionally contain an alert (visual or audio) if the pressure exceeds some critical value (e.g. −30 cm H20 indicating that too much fluid has been removed and the patient is at risk for reexpansion pulmonary edema). This value may be preprogrammed, or selectable by the user.

Compartment Pressure Monitoring (Abdominal or limb): Compartmental syndrome is a medical emergency caused when the pressure in a closed body space (like the forearm, leg, or abdomen) increases to the point where the blood flow is compromised. If left untreated, compartmental syndrome can lead to amputation of the limb, multi-organ failure, or even death. The diagnosis of compartmental syndrome is made by inserting a needle into the compartmental and measuring the pressure. However, the diagnosis is often missed or delayed, and irreversible muscle-damage begins as soon as three hours after the initial injury. A commonly cited reason for the missed diagnosis is failure to measure the pressure. A recent survey noted that half of the participating departments did not have tools capable of measuring compartmental pressure. Current devices are expensive, not disposable, and consequently not available to all physicians. The current device will provide a sterile, disposable, lightweight, inexpensive, compact, self-contained pressure sensor with integrated display that can be used to measure the compartment pressure.

Wireless Monitoring: In one embodiment, a device of the present invention can be coupled wirelessly to one or more graphical displays positioned remotely from the device, thereby enabling wireless monitoring of signal detection with the device. As an example, portable ultrasound is often used for guiding needles during the placement of central venous catheters. During a typical central line procedure, a physician might be splitting his attention between the needle/detection device assembly and the ultrasound screen. The detection device could have both a local display and also transmit data (e.g. pressure data) wirelessly to the ultrasound monitor. The ultrasound monitor would contain an area to display the pressure data along with the ultrasound image.

As another example, the data from the detection device can be transmitted wirelessly to a storage unit, allowing storage and later retrieval of the data. Such storage and retrieval might be utilized, for example, for quality control, diagnostic, or research purposes. For example, the storage unit could save opening pressures during lumbar puncture procedures. A time stamp or the serial number of the particular pressure transducer could assist with identifying the data at a later time. Detection data can be collected and processed, and then utilized to update or reconfigure programming in new and/or existing devices, e.g., for improved performance.

A wireless system could also be used to change display monitors without the need to move additional hardware, such as bulky wires. For instance, a dongle or other type of wireless receiver could receive data from the device and convert the wireless signal to a standard electrical output signal (e.g. 5 µV/mm Hg) to impute to a remote monitor. If a patient is transported, the dongle could be moved from a permanent monitor to a portable monitor for transport, and then plugged into a second permanent remote monitor once the patient reaches the new destination. Alternatively, the LCD on the device could be used during transport, obviating the need for a separate transport monitor. The data could also be directly transmitted to an alternate wireless device, such as a PDA device, without the need for a dongle. Special software could register the disposable pressure sensor to the dongle or device to avoid cross-talk between multiple pressure sensor/wireless receiver units. Alternatively, the dongle and pressure sensor could come together in a disposable pouch and be pre-registered to avoid crosstalk or other type.

The above applications and indications are provided for exemplary purposes. The indications disclosed herein will not be limiting, and the present invention will find use in a variety of additional applications.

Devices can be configured for a single application or for multiple different applications. A device may include a button or switch to allow the device algorithm and display to transition from one indication (e.g. central line insertion) to the next (e.g. lumbar puncture). This transition might include scaling the bar graph, changing the display units (mm Hg to cm H20), changing the display rate, etc. an indicator will alert the user to what mode the device is in. Alternately, the device could automatically change modes by monitoring the pressure readings (e.g. autoscaling the bar graph or changing modes based on the magnitude of the pressure and/or the rate of change in the pressure). For example, a pressure changing from 60 mm Hg to 120 m Hg at 1 Hz might indicate an artery, a pressure changing from 0 mm hg to 20 mm Hg at 1 Hz might indicate a vein or the CSF space, and a constant pressure of 10 mm Hg might indicate a compartment.

In yet another embodiment, the device can contain alert means, such as indicators (visual or audio) that trigger when certain pressure ranges are encountered (e.g. an artery indicator might activate when the mean pressure in the device is over 60 mm Hg and the pressure fluctuates by at least 20 mm Hg over a 1 second period). The alerts could also activate if the needle or catheter is removed from a pressurized fluid (e.g. a "needle dislodgement" indicator might activate if the pressure changes from a value over 20 mm Hg to a constant value less than 5 mm Hg). The device can also have user set alerts (e.g. a button can be pushed when the pressure is 15 mm Hg. The button activates an alert trigger the alerts the user if the pressure changes by more than 5 mm Hg from the pressure value at the time the button was pushed (15 mm Hg). The device could have colored LED's (or distinct audio tones) that indicate certain pressure ranges (e.g. yellow for pressure less than 5 mm Hg, green for pressures between 6 and 30 mm Hg, and red for pressure in excess of 31 mm Hg).

It is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those which may be expressly set forth. Accordingly, the present invention is intended to be described solely by reference to the appended claims, and not limited to the preferred embodiments disclosed herein.

What is claimed is:

1. A device for detecting pressure in a target anatomical environment including a tissue of a patient, the device comprising:

a self-contained housing containing a power source and having a distal portion with a probe extending away from the distal portion at a probe access and having a distal end-most tip portion that is fixed relative to a probe portion adjacent the distal portion of the housing, the housing being untethered such that a proximal portion is closed and does not include a port opening that provides access to an interior of the housing such that the probe access is the only opening into the housing, the housing graspable with a hand of a user to advance the housing and the probe toward the tissue, wherein the probe is a non-hollow probe such that fluid does not flow from a distal tip of the probe to the housing;

a tissue pressure sensing system at least partially carried by the housing and comprising a processing unit coupled with a pressure sensor, the processing unit configured to receive tissue pressure signals comprising a series of instantaneous tissue pressure values from the pressure sensor and determine from the received signals a mean tissue pressure value over a predetermined period of time with a moving average of the series, the mean tissue pressure value indicative of a tissue environment about the distal portion of the probe, the predetermined period of time selected such that the mean tissue pressure value is indicative of a pressure at the distal portion of the probe in tissue; and an output unit carried by the housing and comprising a visual display, the output unit coupled to the pressure sensing system so as to receive the mean tissue pressure value and output to the visual display a reporting signal indicating the determined mean tissue pressure value, wherein the probe is a needle.

2. The device of claim 1 wherein the reporting signal is continuously updated in real time or near real time.

3. The device of claim 1 wherein the mean pressure value is determined by averaging a series of instantaneous pressure values sensed by the pressure sensor.

4. A method for detecting pressure at a probe in a target anatomical environment including a tissue of a patient, comprising:

providing a device comprising a self-contained housing containing a power source and having a proximal portion and a distal portion, the housing being untethered such that the proximal portion that is closed and does not include a port opening that provides access to an interior of the housing, the probe extending away from the distal portion at a probe access and having a distal end-most tip portion that is fixed relative to a probe portion adjacent the distal portion of the housing, the probe access the only opening into the housing, the probe being a non-hollow probe such that fluid does not flow from a distal tip of the probe to the housing, the device further comprising:

a tissue pressure sensing system at least partially carried by the housing and comprising a processing unit coupled with a pressure sensor, the processing unit configured to receive tissue pressure signals comprising a series of instantaneous tissue pressure values from the pressure sensor and determine a mean tissue pressure value over a predetermined period of time with a moving average of the series, the mean tissue pressure value indicative of a tissue environment about a distal portion of the probe; and an output unit carried by the housing and comprising a visual display, the output unit coupled to the pressure sensing system so as to receive the mean tissue pressure value signal and output to the visual display the determined mean tissue pressure value;

advancing the output unit and the probe distally such that the distal end-most tip portion of the probe advances through the tissue of the patient with the mean tissue pressure shown on the visual display; and detecting a change in the mean tissue pressure value about the distal portion of the probe, wherein the probe is a needle.

5. A medical device for a target anatomical environment, the medical device comprising:

a self-contained housing containing a power source and having a distal portion with a probe extending therefrom at a probe access and having a distal end-most tip portion that is fixed relative to a probe portion adjacent the distal portion of the housing, and a proximal portion, the housing being untethered such that the proximal portion does not include a port opening that provides access to an interior of the housing such that the probe access is the only opening into the housing, the housing graspable by a user to manipulate the housing and the probe, wherein the probe is a non-hollow probe such that fluid does not flow from the distal end-most tip portion of the probe to the housing;

a pressure sensing system including a pressure sensor and a processing unit coupled with the pressure sensor, the pressure sensor configured to be carried by the probe, the processing unit carried by the housing and configured to receive input signals from the pressure sensor; and an output unit coupled to the processing unit and carried by the housing, the output unit configured to output a reporting signal to a display, the reporting signal indicative of a pressure at the pressure sensor, wherein the probe is a needle.

6. The medical device of claim 5 wherein the pressure sensor is disposed proximate a distal end of the probe.

7. The medical device of claim 5 wherein the pressure sensor is disposed on a line that is carried by the probe.

8. The medical device of claim 7 wherein the line is detachably carried by the probe.

9. The medical device of claim 5 wherein the housing is detachably coupled to a flexible line.

10. The medical device of claim 5 wherein the power source is operatively coupled to the processing unit and the output unit.

11. The medical device of claim 5 wherein the pressure sensor is a piezoelectric transducer.

12. The medical device of claim 5 further comprising communication circuitry for wirelessly transferring a signal to a remote device.

13. A method for compartment pressure monitoring at a target anatomical environment, the method comprising:

providing a device including:

a self-contained housing containing a power source and having a distal portion with a probe extending therefrom at a probe access and having a distal end-most tip portion that is fixed relative to a probe portion adjacent the distal portion of the housing, the housing being untethered such that a proximal portion is closed and does not include a port opening that provides access to an interior of the housing such that the probe access is the only opening into the housing, the housing graspable by a user to manipulate the housing and the probe, the probe being a non-hollow probe such that fluid does not flow from a distal tip of the probe to the housing;

a pressure sensing system including a pressure sensor and a processing unit coupled with the pressure sensor, the pressure sensor configured to be carried by the probe external the housing, the processing unit carried by the housing and configured to receive input signals from the pressure sensor; and an output unit coupled to the processing unit and carried by the housing, the output unit configured to output a reporting signal to a display, the reporting signal indicative of a pressure at the pressure sensor;

advancing the housing and the probe distally such that the distal end-most tip portion of the probe advances through tissue of a patient;

removing the probe from the tissue; and detecting a change in the pressure sensor within the tissue, wherein the probe is a needle.

14. The method of claim 13 further comprising:

wirelessly transferring, from communication circuitry of the device, a signal to a remote device.

15. The method of claim 14 further comprising:

at the remote device, displaying an indication of a pressure at the pressure sensor.

16. The method of claim 13 further comprising:

continuously updating a reporting signal in real time or near real time.

* * * * *